(12) United States Patent
Ben-Haim et al.

(10) Patent No.: US 11,986,664 B2
(45) Date of Patent: *May 21, 2024

(54) SIMPLE CONTROL OF COMPLEX BIO-IMPLANTS

(71) Applicant: Impulse Dynamics NV, Willemstad (CW)

(72) Inventors: Shlomo Ben-Haim, Milan (IT); David Prutchi, Voorhees, NJ (US); Yuval Ben-Haim, Marlow (GB)

(73) Assignee: Impulse Dynamics NV, Willemstad (CW)

( * ) Notice: Subject to any disclaimer, the term of this patent is extended or adjusted under 35 U.S.C. 154(b) by 82 days.

This patent is subject to a terminal disclaimer.

(21) Appl. No.: 17/334,860

(22) Filed: May 31, 2021

(65) Prior Publication Data
US 2021/0283408 A1    Sep. 16, 2021

Related U.S. Application Data

(63) Continuation of application No. 16/257,125, filed on Jan. 25, 2019, now Pat. No. 11,020,598, which is a
(Continued)

(51) Int. Cl.
*A61N 1/00* (2006.01)
*A61M 5/172* (2006.01)
(Continued)

(52) U.S. Cl.
CPC ......... *A61N 1/37282* (2013.01); *A61M 5/172* (2013.01); *A61M 60/148* (2021.01);
(Continued)

(58) Field of Classification Search
CPC ............ A61N 1/37254; A61N 1/37252; A61N 1/37282; A61N 1/025; A61N 1/36007;
(Continued)

(56) References Cited

U.S. PATENT DOCUMENTS

| 4,958,632 | A |   | 9/1990 | Duggan |
| 5,733,313 | A | * | 3/1998 | Barreras, Sr. ........ A61N 1/3787 |
|   |   |   |   | 128/903 |

(Continued)

FOREIGN PATENT DOCUMENTS

| WO | WO 00/53257 | 9/2000 |
| WO | WO 02/38217 | 5/2002 |

(Continued)

OTHER PUBLICATIONS

Communication Pursuant to Article 94(3) EPC dated Aug. 12, 2014 From the European Patent Office Re. Application No. 05718889.8.
(Continued)

*Primary Examiner* — Scott M. Getzow

(57) ABSTRACT

Methods and devices for tying management of an implantable medical device to the activities of a primary care physician are described, including access control, simplified parameter optimization, support for tuning a device in response to the effects of other treatments in parallel, and support for helping a primary physician and a patient work together to tune device configuration to the activity and performance needs of the patient. In some embodiments, a medical device is self-configuring in a device parameter domain, based on inputs provided in a patient performance domain. The self-configuring of the medical device is based, for example, on an automatically applied transformation of inputs derived from patient performance domain observations into changes in the configuration of the medical device which affect technical parameters of its operation.

20 Claims, 19 Drawing Sheets

Related U.S. Application Data continuation of application No. 15/190,451, filed on Jun. 23, 2016, now Pat. No. 10,188,866.

(60) Provisional application No. 62/183,847, filed on Jun. 24, 2015.

(51) Int. Cl.

| | | |
|---|---|---|
| A61M 60/148 | (2021.01) | |
| A61M 60/178 | (2021.01) | |
| A61M 60/508 | (2021.01) | |
| A61N 1/02 | (2006.01) | |
| A61N 1/36 | (2006.01) | |
| A61N 1/362 | (2006.01) | |
| A61N 1/372 | (2006.01) | |
| A61N 1/39 | (2006.01) | |
| A61N 2/00 | (2006.01) | |
| G05B 15/02 | (2006.01) | |
| G16H 20/40 | (2018.01) | |
| G16H 40/40 | (2018.01) | |
| G16H 40/67 | (2018.01) | |
| A61N 7/00 | (2006.01) | |

(52) U.S. Cl.
CPC ........ *A61M 60/178* (2021.01); *A61M 60/508* (2021.01); *A61N 1/025* (2013.01); *A61N 1/36007* (2013.01); *A61N 1/36128* (2013.01); *A61N 1/36132* (2013.01); *A61N 1/362* (2013.01); *A61N 1/3956* (2013.01); *A61N 2/00* (2013.01); *G05B 15/02* (2013.01); *G16H 20/40* (2018.01); *G16H 40/40* (2018.01); *G16H 40/67* (2018.01); *A61N 1/37254* (2017.08); *A61N 2/008* (2013.01); *A61N 7/00* (2013.01)

(58) Field of Classification Search
CPC ............ A61N 1/36128; A61N 1/36132; A61N 1/362; A61N 1/3956; A61N 2/00; A61N 2/008; A61N 7/00; A61M 5/172; A61M 60/148; A61M 60/178; A61M 60/508; A61M 60/20; A61M 60/515; G05B 15/02; G16H 20/40; G16H 40/40; G16H 40/67

See application file for complete search history.

(56) References Cited

U.S. PATENT DOCUMENTS

| | | | |
|---|---|---|---|
| 5,995,872 | A | 11/1999 | Bourgeois |
| 6,073,049 | A | 6/2000 | Alt et al. |
| 6,449,511 | B1 | 9/2002 | Mintchev et al. |
| 6,454,699 | B1 | 9/2002 | Forsell |
| 6,477,424 | B1 | 11/2002 | Thompson et al. |
| 6,564,101 | B1 | 5/2003 | Zikria |
| 10,188,866 | B2 | 1/2019 | Ben-Haim et al. |
| 2002/0077856 | A1* | 6/2002 | Pawlikowski ......... G16H 40/40 705/2 |
| 2004/0199215 | A1* | 10/2004 | Lee ........................ G16H 20/30 607/48 |
| 2005/0071199 | A1 | 3/2005 | Riff |
| 2005/0159789 | A1 | 7/2005 | Brockway et al. |
| 2007/0255176 | A1 | 11/2007 | Rondoni et al. |
| 2008/0300470 | A1 | 12/2008 | Gerber et al. |
| 2009/0063193 | A1* | 3/2009 | Barton .................. A61B 5/349 340/539.11 |
| 2012/0203079 | A1 | 8/2012 | Mclaughlin |
| 2012/0283800 | A1 | 11/2012 | Perryman et al. |
| 2012/0330384 | A1 | 12/2012 | Perryman et al. |
| 2013/0066400 | A1 | 3/2013 | Perryman et al. |
| 2013/0079849 | A1 | 3/2013 | Perryman et al. |
| 2013/0261473 | A1 | 10/2013 | Xi et al. |
| 2016/0250490 | A1 | 9/2016 | Hoffman et al. |
| 2016/0294790 | A1 | 10/2016 | Susan et al. |
| 2017/0246465 | A1 | 8/2017 | Ben-Haim et al. |
| 2019/0151671 | A1 | 5/2019 | Ben-Haim et al. |

FOREIGN PATENT DOCUMENTS

| | | |
|---|---|---|
| WO | WO 02/082968 | 10/2002 |
| WO | WO 2008/022010 | 2/2008 |
| WO | WO 2012/138782 | 10/2012 |
| WO | WO 2015/092747 | 6/2015 |

OTHER PUBLICATIONS

Communication Pursuant to Article 94(3) EPC dated Apr. 17, 2015 From the European Patent Office Re. Application No. 06711180.7.
Communication Relating to the Results of the Partial International Search dated May 28, 2015 From the International Searching Authority Re. Application No. PCT/IB2014/067096.
International Preliminary Report on Patentability dated Jun. 30, 2016 From the International Bureau of WIPO Re. Application No. PCT/IB2014/067096.
International Search Report and the Written Opinion dated Aug. 3, 2015 From the International Searching Authority Re. Application No. PCT/IB2014/067096.
Notice of Allowance dated Feb. 3, 2021 From the US Patent and Trademark Office Re. U.S. Appl. No. 16/257,125. (3 Pages).
Notice of Allowance dated Sep. 18, 2018 From the US Patent and Trademark Office Re. U.S. Appl. No. 15/190,451. (3 pages).
Official Action dated Feb. 5, 2018 From the US Patent and Trademark Office Re. U.S. Appl. No. 15/190,451. (11 pages).
Official Action dated Nov. 7, 2014 From the US Patent and Trademark Office Re. U.S. Appl. No. 11/816,574.
Official Action dated Aug. 10, 2020 from the US Patent and Trademark Office Re. U.S. Appl. No. 16/257,125. (9 pages).
Official Action dated Aug. 20, 2014 From the US Patent and Trademark Office Re. U.S. Appl. No. 13/576,485.
Restriction Official Action dated Oct. 26, 2017 From the US Patent and Trademark Office Re. U.S. Appl. No. 15/190,451. (6 pages).
Summons to Attend Oral Proceedings Pursuant to Rule 115(1) EPC dated Jul. 15, 2014 From the European Patent Office Re. Application No. 02727012.3.
Stimwave "Freedom. Spinal Cord Stimulation System", Stimwave Technologies, Product Sheet, 2013.

* cited by examiner

SIMPLE CONTROL OF COMPLEX BIO-IMPLANTS

RELATED APPLICATION

This application is a continuation of U.S. patent application Ser. No. 16/257,125 filed on Jan. 25, 2019, which is a continuation of U.S. patent application Ser. No. 15/190,451 filed on Jun. 23, 2016, which claims the benefit of priority under 35 USC 119(e) of U.S. Provisional Patent Application No. 62/183,847 filed on Jun. 24, 2015, the contents of which are incorporated herein by reference in their entirety.

FIELD AND BACKGROUND OF THE INVENTION

The present invention, in some embodiments thereof, relates to implantable medical devices and methods and, more particularly, but not exclusively, to devices having complex configuration profiles, which potentially require or benefit from periodic reconfigurations over an extended period of use.

Some classes of implantable medical devices, including pacemakers, defibrillators, neurostimulators and contractility modulation IPG (implantable pulse generator) devices, include programmable features by which an attending doctor adjusts device function. Setup parameters include those for initial device configuration, and/or adjustment to changing patient needs. Some setup parameters dynamically govern device response to sensed information provided to and/or by the device. Some implantable devices log performance and/or sensed data for simultaneous and/or off-line analysis by a physician.

Some of today's devices offer interfaces that contain over hundred different parameters. It is potentially necessary to change many of them at once to bring about a functional adjustment. Moreover, the effects of different parameters potentially interact with one another, increasing configuration complexity. Device function optionally adjusts according to changing patient status and condition.

The device may include sensing functions and/or interface with sensing data, based upon which device function may self-adjust.

Programmable parameters are typically configured in terms of technically defined quantities, for example, voltage, impedance, electrode characteristics, rate of change (slope/first derivative), rate of rate of change (slope of rate of change/second derivative), maximum rate, energy to be delivered, and/or thresholds defining events.

SUMMARY OF THE INVENTION

According to an aspect of some embodiments of the present invention, there is provided a method of adjusting the operation of an implantable medical device, comprising: receiving access to selectively activate from among a plurality of technical parameter sets preconfigured for use with the implantable medical device, wherein the parameter sets are ordered according to their effect on a clinical parameter affected by operation of the device; monitoring the response of the clinical parameter to activation of a first of the preconfigured parameter sets ordered between at least two others of the preconfigured parameter sets; and activating one of the other two preconfigured parameter sets, based on the ordering of the parameter sets, the monitoring of the clinical parameter and a clinical target for the clinical parameter.

According to some embodiments of the invention, receiving access comprises presenting the device with an access token accepted by the device.

According to some embodiments of the invention, the plurality of technical parameter sets was preconfigured after implantation of the implantable medical device within a patient.

According to some embodiments of the invention, the clinical parameter comprises a clinical measure of patient performance.

According to some embodiments of the invention, the clinical parameter comprises self-reported patient performance.

According to some embodiments of the invention, the parameter sets are ordered according to a therapeutic effect of the device.

According to some embodiments of the invention, the parameter sets are ordered according to a side-effect of the device.

According to some embodiments of the invention, the implantable medical device is a stimulator configured for cardiac contractility modulation.

According to some embodiments of the invention, the implantable medical device is a stimulator configured for gastric contractility modulation.

According to some embodiments of the invention, the implantable medical to device is an implanted pulse generator configured for central nervous system stimulation.

According to some embodiments of the invention, the implantable medical device is a stimulator configured for cardiac resynchronization therapy.

According to some embodiments of the invention, the plurality of technical parameter sets are configured by a device implantation specialist, and the receiving access is by a primary medical care provider.

According to some embodiments of the invention, the preconfigured parameter sets are stored by the implantable medical device.

According to some embodiments of the invention, the method comprises continued monitoring of the response of the clinical parameter, and activating of other parameter sets based on the ordering of the parameter sets and as indicated by the state of the monitored clinical parameter relative to the clinical target.

According to some embodiments of the invention, the continued monitoring ends when the clinical parameter reaches the clinical target.

According to an aspect of some embodiments of the present invention, there is provided a method of associating an implanted medical device to a non-implanting referring health care provider, comprising: providing the referring health care provider with a device access key; configuring the implanted medical device to allow at least one function of the device to be controlled based on identification of the device access key.

According to some embodiments of the invention, the at least one accessible function includes selection from a plurality of technical parameter sets preconfigured for use with the implantable medical device.

According to some embodiments of the invention, the configuring comprises receiving an identifier of the device access key from the referring health care provider, and configuring the device to recognize the identifier.

According to some embodiments of the invention, the configuring comprises the referring health care provider configuring the device to recognize an identifier of the device access key.

According to some embodiments of the invention, the at least one accessible function comprises activation of an inactive treatment function of the implanted medical device.

According to some embodiments of the invention, the method comprises locking the device to inactivate the inactive treatment function until accessed by the device access key.

According to some embodiments of the invention, the device access key comprises a charging mechanism for charging the implanted medical device.

According to some embodiments of the invention, the device access key is limited in a number of uses.

According to some embodiments of the invention, the device access key comprises an alphanumeric code.

According to some embodiments of the invention, the device access key comprises a cryptographic key.

According to an aspect of some embodiments of the present invention, there is provided an implantable medical device system supporting configuration by a primary care physician, comprising: a data store configured to receive and store a plurality of inactive technical parameter sets for use with the implantable medical device; and a selection interface for selecting from among the inactive technical parameter sets and activating at least one of them; wherein the implanted medical device provides access allowing parameter set activation based on recognition of an access key.

According to some embodiments of the invention, the data store indexes the technical parameter sets according to a parameter of their effect on patient performance, and the selection interface presents inactive technical parameter sets for selection according to the index.

According to some embodiments of the invention, the data store is integrated with the implanted medical device.

According to some embodiments of the invention, the access key does not give access to modify the inactive technical parameter sets of the data store.

According to some embodiments of the invention, the access key comprises an alphanumerically represented key.

According to some embodiments of the invention, the access key comprises a cryptographic key.

According to some embodiments of the invention, the access key comprises a charger device.

According to some embodiments of the invention, the access key comprises the data store.

According to some embodiments of the invention, operation of the selection interface comprises entering data about the operation of another implantable medical device of the patient.

According to some embodiments of the invention, operation of the selection interface comprises entering data about a medicament prescription of the patient.

According to an aspect of some embodiments of the present invention, there is provided an implantable medical device configured to allow at least one functional profile of the device to be controlled based on identification of a device access key, wherein the device access key grants exclusive access to the functional profile.

According to some embodiments of the invention, control of the functional profile of the device is available based on identification of the device access key.

According to an aspect of some embodiments of the present invention, there is provided a method for associating a primary care physician to a patient having an implanted medical device comprising: referring the patient from the primary care physician to an implanting physician for implanting the implanted medical device; presenting a device access key, thereby obtaining exclusive access to the functions of a functional profile of the implanted medical device after implantation; operating an exclusively accessed function of the implanted medical device to change an operating parameter of the implanted medical device.

According to an aspect of some embodiments of the present invention, there is provided an implantable medical device configured to convert from an unmanaged post-implantation state to a managed post-implantation state upon activation of a state changing function by a primary care physician, wherein the managed post-implantation state allows activation of a treatment function not available in the unmanaged post-implantation state.

According to some embodiments of the invention, the activation comprises presenting an access key to the implantable medical device.

According to some embodiments of the invention, the activation comprises activating a channel reserved for use by a primary care physician.

According to some embodiments of the invention, the device provides an access key to the physician upon activation of the channel, and thereafter allows activation of the treatment function based on presentation of the access key.

According to an aspect of some embodiments of the present invention, there is provided a method of setting a plurality of technical domain parameters of an operating configuration of an implanted medical device, the method comprising: receiving a selection input indicating a target state of at least one parameter in a patient performance domain; converting the selection input to settings of the technical domain parameters; and storing the settings of the technical domain parameters as the operating configuration of the implanted medical device.

According to some embodiments of the invention, the converting comprises selection of technical domain parameters based on observed correlations of operating configurations with effects in the patient performance domain.

According to some embodiments of the invention, the converting comprises using the selection input to select from a data structure comprising a plurality device configuration options.

According to some embodiments of the invention, the selection input indicates the target state by specification of a direction of change for a value of the at least one parameter in the patient performance domain.

According to some embodiments of the invention, the selection input indicates a plurality of the directions of change for values of a corresponding plurality of parameters of the at least one parameter in the patient performance domain.

According to some embodiments of the invention, the converting comprises adjustment of a greater number of parameters in the technical domain than the number of parameters indicated in the patient performance domain by the selection input.

According to some embodiments of the invention, the at least one parameter in the patient performance domain comprises a parameter correlated with the production of a therapeutic effect in the patient by the implanted medical device.

According to some embodiments of the invention, the at least one parameter in the patient performance domain comprises a parameter correlated with the production of a side effect in the patient by the implanted medical device.

According to some embodiments of the invention, the selection input comprises indication of a relative balance of the therapeutic effect and the side effect.

According to some embodiments of the invention, the converting comprises selecting an at least partially predefined device configuration from the device configuration option data, based on the received selection input.

According to some embodiments of the invention, the method comprises repeating the receiving, converting, and storing after a time interval during which the at least one parameter in the patient performance domain changes to reflect operation of the implanted medical device under control of the previously stored operating configuration.

According to an aspect of some embodiments of the present invention, there is provided a method of setting an operating configuration of an implanted medical device for production of a therapeutic effect in a patient, the method comprising: evaluating of a current state of at least one parameter in a patient performance domain; determining a target state of the at least one parameter, based on the evaluating; and providing a machine-encoded selection input indicating the determined target state for conversion into a plurality of technical domain parameter settings defining an operating configuration of the implanted medical device.

According to some embodiments of the invention, the at least one parameter in the patient performance domain comprises a parameter correlated with the production of a therapeutic effect in the patient by the implanted medical device.

According to some embodiments of the invention, the at least one parameter in the patient performance domain comprises a parameter correlated with the to production of a side effect in the patient by the implanted medical device.

According to some embodiments of the invention, the selection input comprises an indication of a relative balance of the therapeutic effect and the side effect.

According to some embodiments of the invention, the conversion comprises selecting an at least partially predefined device configuration from the device configuration option data, based on the received selection input.

According to an aspect of some embodiments of the present invention, there is provided a method of customizing a plurality of configuration options of an medical device implanted in a patient, the method comprising: determining correlations between a plurality of operating configurations of the device and a corresponding plurality of states of at least one patient performance parameter; generating device configuration option data, based on the determined correlations, the device configuration option data being structured to allow selection of an operating configuration option from an indication of a target state of the at least one patient performance parameter; and storing the device configuration option data for use in determination of an actual operating configuration of the implanted medical device, based on selection input indicating a target state of the at least one patient performance parameter.

According to some embodiments of the invention, the method comprises storing an actual operating configuration of the implanted medical device, based on selection input indicating the target state and the device configuration option data; comparing an actual state of the at least one patient performance state to the target state, the actual state being obtained after the determination of the operating configuration, and updating the device configuration option data, based on the comparing.

According to some embodiments of the invention, the determining comprises both: determining some of the correlations individually for the patient, and additional selection of the correlations from one or more previously determined correlations between operating configurations and patient performance parameter states; and the generating comprises using correlations determined individually for the patient as to references to map the additionally selected correlations to the patient performance parameter states of the patient.

According to an aspect of some embodiments of the present invention, there is provided a kit for configuration of an implantable medical device, the kit comprising: A data store configurable to store device configuration option data customized for a patient to indicate correlations between device configuration options and at least one patient performance parameter; A device parameter store configurable to define an operating configuration of the implantable medical device; and a configuration selector, operable to: receive selection input indicating a target state of the at least one patient performance parameter, define an operating configuration of the implantable medical device, based on the received selection input and the device configuration option data in the data store, and provide the defined operating configuration to the device parameter store.

According to some embodiments of the invention, the implantable medical device comprises the parameter store, and the configuration selector.

According to some embodiments of the invention, the implantable medical device at least partially comprises the data store.

According to some embodiments of the invention, the implantable medical device entirely comprises the data store.

According to some embodiments of the invention, operation of the configuration selector to define the operating configuration comprises selecting an at least partially predefined configuration from the device configuration option data, based on the received selection input.

According to some embodiments of the invention, operation of the configuration selector to define the operating configuration comprises defining a parameter of the operating configuration, based on the received selection input.

According to some embodiments of the invention, the indicated target state comprises an increase or decrease in a value measuring the at least one patient parameter.

According to some embodiments of the invention, the selection input indicates the target state by specification of a direction of change for a value of the at least one parameter in the patient performance domain.

According to some embodiments of the invention, the system comprises an interface device, configured to receive user input indicating the target state of the at least one patient performance parameter, and electronically communicate this as the selection input to the configuration selector.

According to some embodiments of the invention, operation of the configuration selector to define the operating configuration comprises selecting an at least partially predefined configuration from the device configuration option data, based on the received selection input.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon.

Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium.

A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
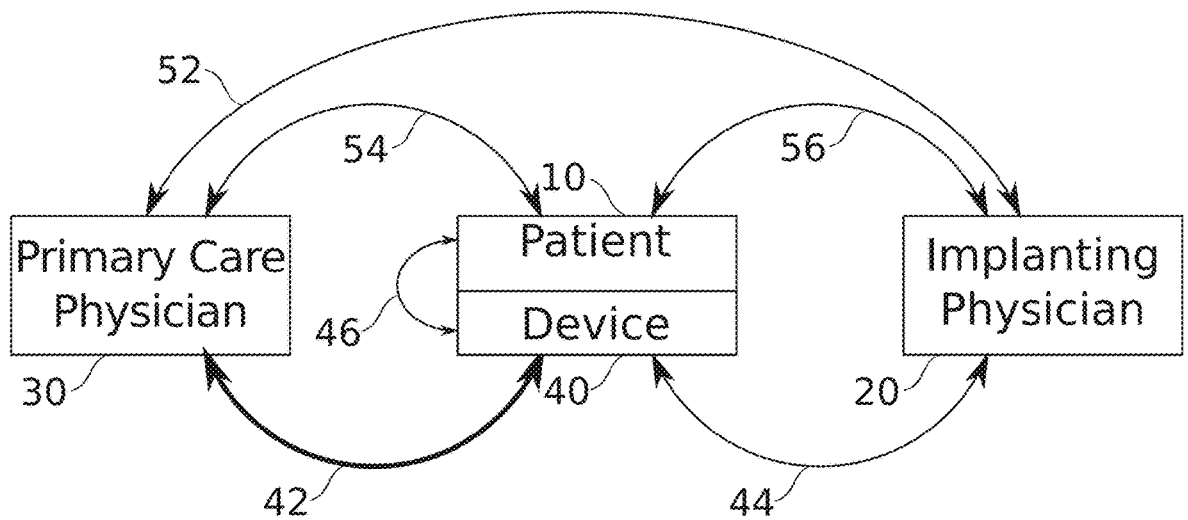
FIG. 1A is a schematic block diagram representing interactions among a patient, an implanted medical device, a primary care physician and/or clinic, and an implanting physician and/or clinic, according to some exemplary embodiments of the invention.

The present invention, in some embodiments thereof, relates to implantable medical devices and methods and, more particularly, but not exclusively, to devices having complex configuration profiles, which potentially require or benefit from periodic reconfigurations over an extended period of use.

Overview

A broad aspect of some embodiments of the invention relates to the assignment of implantable medical device management responsibilities to primary care physicians.

In some embodiments, an implanted medical device comprises a large number of parameters (for example, 100, 200, 500, 600, or another greater, lesser or intermediate number) that need to be configured for correct device function.

Optionally, parameters interact, so that settings are adjusted for several parameters in concert. Optionally, the device is an implantable medical device providing one or more modalities of controlled stimulation (ultrasonic, thermal, electrical, electromagnetic, and/or magnetic stimulation, for example). Examples of stimulus sites are found throughout the body, and include the central nervous system (brain and spinal cord, for example), the peripheral nervous system (the vagus nerve and other cranial and spinal nerves), organs of the endocrine system, the heart, the stomach, and the kidneys. Stimulation treatments include treatments for pain control, affective disorders, cardiac fibrillation, heart failure, cardiac rhythm disorders, diabetes, diabetic obesity, and/or obesity. Parameters of stimulus devices optionally include numerous parameters of, for example, stimulus strength, duration, interval, and/or pulse count. Optionally, any of these is dynamically dependent on physiological parameters, for example as sensed directly by and/or externally provided to the device.

Optionally, an implanted medical device is a non-stimulatory device (for example, a ventricular assist device)

Implanted medical devices optionally sense one or more physiological parameters, for example, in support of a treatment, and/or as a primary function Implanted devices are optionally configurable to deliver a plurality of treatments.

Device complexity tends to exclude non-specialists from meaningfully integrating medical device management into clinical practice. However, primary care physicians are a potentially underutilized resource for the management of such medical devices.

In some embodiments, implanted device features support aspects of an overall clinical system in which primary care physicians assume a more central role in implantable device management. Potentially, this comprises increased referrals by primary care physicians for implanted medical device treatments. Increased referrals could be based, for example, on a primary care physician's greater familiarity with the effects of the devices, and/or on the understanding that a patient will return with options for primary care treatment increased by the new device, rather than as a patient with a device that leaves the primary care provider partially excluded from the clinical picture.

An aspect of some embodiments of the invention relates to implanted medical devices configured with at least one channel of control and/or monitoring for use by a primary care provider (for example, a primary care physician, and/or primary care clinic and its staff). Optionally, the channel is dedicated for use by a primary care provider.

In some embodiments, functions accessed by this channel include, for example, pre-prepared device parameter settings and/or methods of selecting from among them, device functioning and/or sensing reports formatted to assist primary care treatment planning, features that help the primary care physician to balance device-delivered treatments with other ongoing treatments and their effects, and/or features that facilitate communication between a primary care physician and specialist health care providers.

In some embodiments, a device comprises a channel of control designated for use by a primary care physician. Optionally, the channel is configured for primary care use by a device implanter and/or clinic, for example during initial device setup at the time of implantation. In some embodiments, other channels are provided for use by, for example, a payer (such as insurer or HMO) or medical specialist. In some embodiments, the group of functions available through a channel of control comprise a functional profile.

In some embodiments, control by the primary care provider is in a "patient performance domain", wherein device domain parameters ("low level" parameters) are set in concert (for example, by selecting a predefined parameter set, or otherwise set without detailed specification of device operation) according to measurements and/or indications of observed and/or intended medical results. For example, balancing a therapeutic effect of a device with side-effects affects large number of parameters in the device domain. In some embodiments, control of this balance is by selecting "larger therapeutic effect" or "less side-effects", while the detailed parameter adjustments at the device parameter level are transparent to the primary care provider; performed, for example, according to some predetermined and/or previous calibrated scheme. A predefined parameter set optionally includes any full or partial group of settings which specify device domain parameters, but is not necessarily active on the implanted device.

A predefined parameter set is optionally predefined by specifying one or more ranges along which parameters are allowed to vary.

Optionally, a predefined parameter set is associated with an expected clinical effect, for example, an effect on a clinical parameter. Herein, the term "clinical parameter" is used interchangeably with the term "patient performance parameter" to optionally include any clinical observation of a patient; for example, a test result to (e.g., metabolite level, imaging data, and/or monitoring data), a symptom, and/or another clinical finding. The expected clinical effect is optionally specified at least in part with respect to another predefined parameter set. For example, a therapeutic effect, side-effect, rate, and/or concentration is expected to be larger or smaller than the corresponding metric for another parameter set. Optionally, the expectation is only that there is a difference, according to an ordering of the parameter sets. For example, of three or more parameter sets which comprise a monotonic change in one or more parameters, a middle one is optionally "larger" in an effect on some clinical parameter than either of the other parameter sets.

In some embodiments, control by the primary care provider is in another domain abstracted from the lowest-level device parameter domain. For example, a device is set up to deliver "doses" of a therapy, and control by the primary care physician comprises, for example, choosing a particular dose "formulation" (parameter setup), number of dose deliveries, and/or frequency of dose delivery.

In some embodiments, a plurality of predetermined options corresponding to potential treatment outcomes is defined, each choice entailing different device domain parameters; and selection from within the range is allowed to a primary care provider. This is a potential advantage to use the relatively detailed knowledge a primary care provider has of a patient's health, without requiring detailed knowledge of the device itself.

In some embodiments, a primary care provider guides and/or monitors "A-B" type optimizations of device parameters. In some embodiments, there is a plurality of setting ranges each varying between different measures of, for example, patient performance, side-effects, and/or therapeutic effects. Optionally, the choice of which range should be adjusted is given to the primary care physician.

An aspect of some embodiments of the invention relates to implanted medical devices configured to provide controlled access to a primary care provider.

In some embodiments of the current invention, implanted medical device features link a primary care provider (a physician, a clinic, or another medical provider) to an implantable medical device. Optionally, the link comprises granting a primary care provider identifier-controlled access to one or more of the device to functions. Optionally, the identifier-controlled access is exclusive to a particular primary care provider (group or individual). Optionally, the link comprises use by the primary care physician of a device or system component (for example, a device charger, or a data store containing device configuration data).

In some embodiments, primary care management of a device requires use of a designated access control number or device (such as a password, identifying numeric key, physical device, or another access control token). Herein, any such access control token is interchangeably referred to as a "key".

Different regimes of access control comprise embodiments of the invention. In some embodiments, only a primary care provider who has a key issued by the implanting physician is able to access the device as a primary care provider.

A potential advantage of such access control is to allow an implanting physician to maintain quality control and/or monitoring over the third-party operation (for example, operation by a primary care physician) of devices for which the implanting physician is responsible. Keys are optionally issued per device and/or per device group (for example, all devices implanted by a particular implanting physician). Alternatively, a key is initially assigned by a referring primary care physician, and assigned to the device by the device implanter.

Additionally or alternatively, a primary care physician uses an existing key to "unlock" a device when a patient comes under the care of his clinic, thereby assuming access to an available control interface. Optionally, an exclusive association is enforced, unless, for example, unless the original implanter removes association. In some embodiments, in particular, a functional profile comprising functions for use by a primary care provider is exclusively available in response to recognition of a single key.

Alternatively, any physician possessed of an appropriate key can access the device. Optionally, a physician is able to determine whether another physician is accessing the device. Exclusive and/or verified access is a potential advantage, in that a primary care physician becomes thereby "attached" to the device (potentially promoting traceability and/or consistency of care, for example). In some embodiments, for example, with devices that supply an elective treatment, primary care physician access control provides a mechanism for dose regulation.

For example, a patient purchases a treatment regime that is supplied, monitored and/or adjusted based on access provided by a particular key and/or key group.

In some embodiments, another arrangement for providing and controlling physician access to a device is made. Optionally, the degree of exclusivity provided by the access mechanism is chosen according to any appropriate combination of controlling conditions, for example, market, liability, and/or regulatory conditions.

An aspect of some embodiments of the current invention relates to control of an implanted medical device based on the administration of another synergistic antagonistic, or otherwise interacting auxiliary treatment ("auxiliary treatment" as used herein means any treatment that is not that of the implanted medical device itself, and does not imply that the implanted medical device therapy be dominant to the other treatment).

In some embodiments of the invention, an implanted medical device is provided with one or more alternate device parameter sets that are calibrated to alter delivery of a device therapy in response to measured and/or predicted therapeutic and/or side effects of one or more other treatments (auxiliary treatments). Selection and/or tuning of parameter sets is performed by the primary care physician, based on the overall treatment regime of the patient.

A potential benefit of providing cross-treatment responsiveness to an implanted medical device is to assist a primary care physician in integrating a plurality of simultaneous therapies.

An aspect of some embodiments of the current invention relates to medical devices which are self-configuring in a device parameter domain, based on inputs provided in a patient performance domain. Optionally, the medical device comprises an implanted medical device; for example, a pacemaker, implantable cardioverter defibrillator (ICD), cardiac resynchronization therapy device (CRT-D), left ventricular assist device (LVAD) neurostimulator and/or contractility modulation IPG (implanted pulse generator).

In some embodiments, the self-configuring of the medical device is based on an automatically applied transformation of inputs derived from patient performance domain observations into changes in the configuration of the medical device which affect technical parameters of its operation. Such a technical parameter optionally comprises, for example, a voltage, impedance, electrode characteristic, rate of change (slope/first derivative), rate of rate of change (slope of rate of change/second derivative), maximum rate, energy to be delivered, and/or thresholds defining events.

Herein, a group of such technical parameters, taken together, defines a technical parameter domain; conversely, the parameters are said to be within a technical domain. An operating configuration for a device comprises a selection of settings for parameters within a technical domain.

In some embodiments, the transformation comprises direct manipulation of a selected subset of parameters in the device parameter domain, which are determined to correlate in their values to effects produced in the patient performance domain. In some embodiments, the transformation comprises selection of a device configuration option describing the settings of a plurality of device parameters. The selection is optionally of a predetermined device configuration, or of a device configuration arrived at by application of one or more rules associating the patient parameter domain to the device parameter domain, via data describing options for device configuration.

A potential advantage of the self-configuring is to allow a non-specialist medical practitioner, familiar with evaluation in the patient performance domain, to perform adjustments to the medical device. This is optionally without manipulation of or familiarity with the low-level configuration details of the medical device.

Potentially, this allows the device to be tuned to the conditions of an individual patient, without constant involvement of specialist medical personnel, and/or in the course of routine primary medical care of the patient.

Features of certain rate-responsive cardiac pacemakers provide an example of the complexity potentially accompanying implantable medical device configuration.

Such cardiac pacemakers are configurable to recognize bodily motion and change the heart rate accordingly. Suitably configured, this allows a patient to perform exercise that increases cardiac demand—and have the cardiac output increase to meet it, while remaining under suitable pacing control by the device.

A pacemaker with a rate responsive feature optionally uses deformation of a piezoelectric crystal to detect acceleration. Definition of how control of how pacing (and thus, heart rate) should respond to an acceleration event optionally includes the definition of parameters from the following (non-exhaustive) list:
1. A minimal amplitude of acceleration marking possible event onset.
2. One or more event onset validation parameters, for example, a major frequency component, a minor frequency component, and/or a frequency modulation criterion.
3. A duration of acceleration that confirms the event.
4. Parameters governing trend monitoring during confirmed events, defined for one or more classifications; for example as minimum percent rise in acceleration, and duration of trend sampling time.
5. Parameters defining response to a trend-classified event; for example: latency to response, time slope of pacing rate increase, maximal heart rate, dependency of time slope on acceleration trend, and/or dependency of maximum heart rate on acceleration trend.

It should be noted that not only are many parameters described in the foregoing list, these parameters also potentially interact with one another. For example, if acceleration trend determination is adjusted to become more responsive, it may also become prone to noise; this may require reduction in response time slope in order to reduce incidence of spurious pacing increases. Management of this complexity generally is outside the domain of a non-specialist.

Optionally, however, a primary physician can become familiar with the general effects associated with rate-responsive cardiac pacemakers in the patient domain (e.g., greater range of allowable exertion, traded against possible triggering of events such as atrial fibrillation). In some embodiments, this knowledge is sufficient to allow selection of the operating configuration of a suitably prepared medical device.

Patient performance parameters optionally include any observation of a patient; for example, a test result (e.g., metabolite level, imaging data, and/or monitoring data), a symptom, and/or another clinical finding. A patient performance parameter optionally comprises measurement of a response to exercise, food consumption or fasting, drug injection, or another manipulation. Other examples of patient performance parameters include, for example, exercise tolerance, pain, shortness of breath, dizziness, weight loss, and/or water retention.

An aspect of some embodiments of the current invention relates to medical devices which are at least partially self-training for determination of a relationship between a device parameter domain and a patient performance domain. In some embodiments, a device operates to receive sensed patient performance data, and determines a correlation of the data with a current and/or recent configuration of the device in a device parameter domain. Optionally, configuration of the device in response to this correlation comprises adjustment of a configuration change response to control inputs, so that a predictable relationship between control input and patient performance is established, maintained, and/or restored.

Sensed patient data optionally comprise, for example, activity level (accelerometer-derived, for example), heart rate, electrocardiogram wave from, temperature, respiratory rate, blood metabolite level (for example, glucose), or another sensed parameter.

It is to be understood the descriptions provided herein in terms of domains and/or spaces are not referring to literal volumes, nor to mathematical abstractions as such; rather, such descriptions are ways of describing and/or conceptualizing certain realized features of some embodiments of the present invention.

It should also be noted that reference is also made herein to devices comprising representations of more than one domain/space of any given type.

For example, a device parameter domain is optionally defined by the ranges of settings which can be adopted by particular control elements (registers, for example) of a medical device. Insofar as settings in this domain are ordered with respect to one another (or otherwise provided with structural relationships), they are optionally also considered to define a device parameter space. In some embodiments, it is appropriate to consider a sub-domain of a whole device parameter domain, and/or to consider the device as comprising settings which define two separate device parameter domains.

A patient performance domain is optionally defined in the first instance by one or more patient observables (which are observable to obtain an observation result such as a test result, symptom, and/or another clinical finding). Insofar as different observation results are relatable to each other, for example, according to an order, they optionally comprise a patient performance space. Preferably, observables are affected by operation of the medical device. There is optionally more than one patient performance domain to consider—for example, two observables may be equivalent in their relationship to the configuration of the device, or equivalent after a suitable transformation.

In some embodiments, an appropriately programmed medical device at least partially embodies a description of a patient performance domain, insofar as it is capable of receiving input closely derived from patient observables, and then reconfiguring itself to produce substantially predictable effects on those same observables, and/or on other patient observables. In some embodiments, this capability for reconfiguration relies on a transformation (such as a mapping) that can be applied between the patient performance domain, and the device parameter domain.

In some embodiments, moreover, it is useful to distinguish a control domain (or space). This is the domain in which the medical device receives its inputs. Except as may be otherwise explicitly indicated herein, "control domain" and/or "control space" are used with particular reference to inputs having a direct (or other simple) relationship to some patient performance domain. There may be more than one such control space available.

In an example of what should be understood as a simple relationship between a control space and a patient performance space: a control space may comprise discrete control states selectable by the pressing of buttons, for example, two buttons to such as "+" and "−", for movement of a selected control state up and down in an order of such states. States of a corresponding patient performance domain as such, however, optionally are not be themselves discrete, optionally comprise more or fewer observables (axes, in some embodiments) than the control space exposes, and/or otherwise differ from strict one-to-one correspondence to the control domain. However, even with such caveats in view, it will be generally appreciated that a selection in control space may have a clear and direct correlate in patient performance space: for example, the "+" button optionally corresponds to an increase in both a treatment effect and a side-effect, and the "−" button to a decrease in both. Accordingly, the control domain/space and the patient performance domain/space are sometimes referred to herein in combination as comprising a patient performance space or domain.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Interactions Between Patient, Different Care Providers, and Implanted Device

Reference is now made to FIG. 1A, which is a schematic block diagram representing interactions among a patient 10, an implanted medical device 40, a primary care physician and/or clinic 30, and an implanting physician and/or clinic 20, according to some exemplary embodiments of the invention.

The double-headed arrows 42, 44, 46, 54, 56, 52 represent different pairwise interactions between agents in relation to an implantable medical device: a patient 10, a primary care physician (and/or clinic and staff) 30, a device implanting physician (and/or clinic and staff) 20, and the implantable medical device 40 itself.

The expertise and personal patient knowledge of primary care physicians is a valuable and efficient resource. Typically, however, direct interaction 42 between a primary care physician 30 and an implanted device 40 is rare or unavailable. The role of a primary care physician in device 40 management is often relegated to indirect actions, for example, initial referral to and occasional consultation with an implanting physician 20 along interaction route 52. Factors contributing to this limitation potentially include:

- There is no direct control of the device 40 given to the primary care physician 30;
- Mastering the complexity of the device 40 is not within the scope of the primary care physician's knowledge and/or duties;
- Once the device 40 is implanted, a key aspect of the patient's health becomes the domain of a specialist, and the primary care physician 30 may substantially be excluded from this piece of the clinical picture.

In some embodiments of the current invention, an implantable medical device comprises features that potentially enhance the ability of a primary care physician to participate in the ongoing management and monitoring of the device, turning primary care-implantable device interactions 42 into an important part of the patient's care. Potential advantages for increased association of a primary care physician 30 with an implanted medical device 40 of a patient include:

- Increased communication with the patient, in frequency and/or over time, to guide personalization of device operation;
- Lower threshold of need and/or more frequent opportunities to adjust device operation;
- Adaptive integration of device operation with other medical treatments; and/or
- Use of device monitoring features (for example, sensor data provided live and/or logged, and device status and/or activity logs) to guide an overall patient treatment regimen, that optionally includes one or more other devices and/or drug treatments.

Figure 1B:
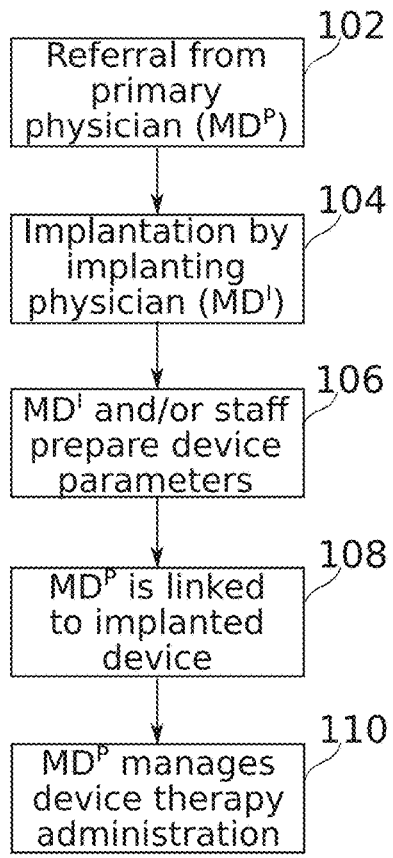
FIG. 1B is a schematic flowchart of how a primary care physician ($MD^P$) interacts with an implantable medical device, according to some exemplary embodiments of the invention.

Reference is now made to FIG. 1B, which is a schematic flowchart of how a primary care physician ($MD^P$) interacts with an implantable medical device, according to some exemplary embodiments of the invention.

At block 102, in some embodiments, $MD^P$ determines that an implanted medical device is of potential benefit to a patient, and makes a referral to an implanting physician accordingly. In this example, the device is an implanted pulse generating device (IPG) for the sake of illustration; for example, a device for delivery of cardiac contractility modulation (CCM), gastric contractility modulation (GCM); for deep brain, spinal, or other central nervous system stimulation; and/or peripheral nervous system stimulation. However, it is to be understood that in some embodiments, another type of implantable medical device is the object of the method, for example, a ventricular assist device (VAD) or implantable cardioverter-defibrillator (ICD).

At block 104, in some embodiments, the device is implanted by an implanting physician (MD) and/or associated clinic and staff.

At block 106, in some embodiments, the $MD^P$ and/or associated clinic and staff prepare a device for the situation of the individual patient. For a typical device, preparation includes determining the relationship between the operational parameters of the implantable device, and their effects on the patient Implantable device parameters are potentially controlled by up to several hundred different device settings. Optionally, a plurality of parameter sets is prepared to cover future medical and treatment eventualities. For example, treatment parameters are determined having greater or lesser therapeutic effects, different balances of therapeutic effect to side-effect, different assumptions about the therapeutic environment of the device (other ongoing treatments), and/or different thresholds to prevent incorrect activation of the device.

At block 108, in some embodiments, the ($MD^P$) is linked to the implanted device. Linkage of $MD^P$ and device is optionally by one or more of the following methods, or by another method:

- The $MD^P$ has, supplies, is given control over, and/or is provided access to a device component (for example, a device charger, or a data store containing device configuration data) that is required for operation of a therapeutic function of the implanted medical device.
- The $MD^P$ has a code (for example, a cryptographic key, alphanumeric code), or another identifying token, comprising a key to which the implanted medical device is programmed to allow access for activating and/or modifying a function of the device (for example, a monitoring function or a therapeutic function).

In the case of an identifying token, there are different options for creating a token-to-device association. These include, for example, one or more of the following:

- The token is previously assigned to the $MD^P$ (for example, by a device manufacturer), provided by $MD^P$ along with the referral, and recognition of the token is programmed into the implanted device by the $MD^P$ as part of the implantation and configuration procedure.
- Recognition of the token is programmed into the implanted device by the $MD^I$, as part of the implantation and configuration procedure. The token is provided by the $MD^I$ to a patient to give to his $MD^P$ and/or provided directly to a referring $MD^P$.
- The token is previously assigned to the $MD^P$ (for example, by a device manufacturer). The device recognizes the token as valid upon first presentation (for example, when a patient first visits the $MD^P$ post-implantation). Optionally, primary care functions of the implanted device are exclusively associated with that token thereafter. The association is optionally transferable and/or non-exclusive.
- The device itself provides a token (cryptographic key, password, or other information) upon correct interrogation by an $MD^P$, and thereafter access to the implanted device is allowed upon presentation of the provided token.

Optionally, there is a plurality of access tokens, each associated with an implanted medical device, either individually or as a group. Optionally, each access token provides access to some or all of the device functionality intended for use by a primary care physician. Optionally, acceptance of an access token by the device is permanent or temporary (for example, time or use limited). For example, a token providing access to logging features of the device is permanent, a token providing to access to initiate a therapeutic regime is time limited (for example, to help ensure that the device is not operated beyond the due date of a designated periodic maintenance check), and/or a token providing access to specialist consultation features of the device is use limited (for example, for controlling access to device services such as a post-implantation follow up with an implantable device specialist).

At block 110, in some embodiments, the $MD^P$ manages device therapy administration, corresponding to the interactions of interaction arrow 42. Optionally, primary care device management occurs during regular checkups, and/or other visits of a patient to a primary care provider.

In some embodiments, implanted device operations are packaged for the primary care provider in terms of "doses", and/or otherwise simplified relative to the large number of programmable parameters that a device natively presents.

Optionally, medical device operation by a primary care physician is modeled on a "prescription"-type model, wherein one or more aspects of the operation of the device are mapped to provider concepts that are conventionally used for pharmaceuticals. For example, with the increased range and/or availability of therapeutic functions in implantable medical devices, there is a potential for devices to overlap in their treatment indications with pharmaceutical medicaments that are ordinarily prescribed and/or monitored at the level of primary care.

In some embodiments, a treatment regime that is pre-prepared for availability from an implanted medical device (a stimulus regime, for example) is selected by a primary care physician to run for a certain period of time, a certain frequency, and/or with a certain strength of stimulation or other measure of therapeutic effect intensity.

For example, a cardiac contractility modulation (CCM) device is configured to run for a certain number of hours per day.

Additionally or alternatively, settings of a device provide alternatives (optionally, gradated alternatives) between two or more states that differentially affect patient performance parameters and/or side-effects. For example, stabilization of an organ function (such as heart rate, endocrine secretion rate, nerve activity level, and/or kidney efficiency) is balanced differently in two or more settings against retaining the organ's ability to meet dynamic demands on it due, for example, to changing activity, health, and/or effects of other treatments. A more stable setting potentially provides more health safety, such as a lowered risk of decompensation, while a more dynamic setting potentially enables a more normal lifestyle.

Potentially, this kind of simplification makes it easier for a primary care physician to evaluate the effects and benefits of an implanted medical device in terms that can be more easily understood in relation to pharmaceutical medicaments.

Equipping a primary care physician with this perspective may help the physician to accept, and even encourage, the use of an implantable medical device as part of an overall therapeutic regimen for disease treatment and management.

In some embodiments of the invention, features of an implantable medical device that tie it into operations performed and/or selected in the context of primary care also serve to support business and clinical infrastructure aspects of implantable medical devices. Such aspects include, for example, sales and distribution, technical support, billing and insurance reimbursement, and medical training. It is to be understood that some of these aspects potentially behave synergistically with respect to features that tie a device to a primary care physician. For example, greater familiarity with a device and its effects (achieved, for example, at block 110 of FIG. 1B), potentially encourages $MD^P$ to make future referrals at block 102.

Understanding by $MD^P$ that the patient will return with the options for future treatment enhanced, rather than locked away in an inaccessible device, may also encourage referrals. The implanting physician 20 and device supply chain also potentially benefit from wider familiarity with and acceptance of the device in the wider medical community. Where use of an implanted medical device is associated with decreased costs at the point of treatment, and/or in the medical system overall, there are potential benefits for payers in reducing barriers to device deployment.

Figure 1C:
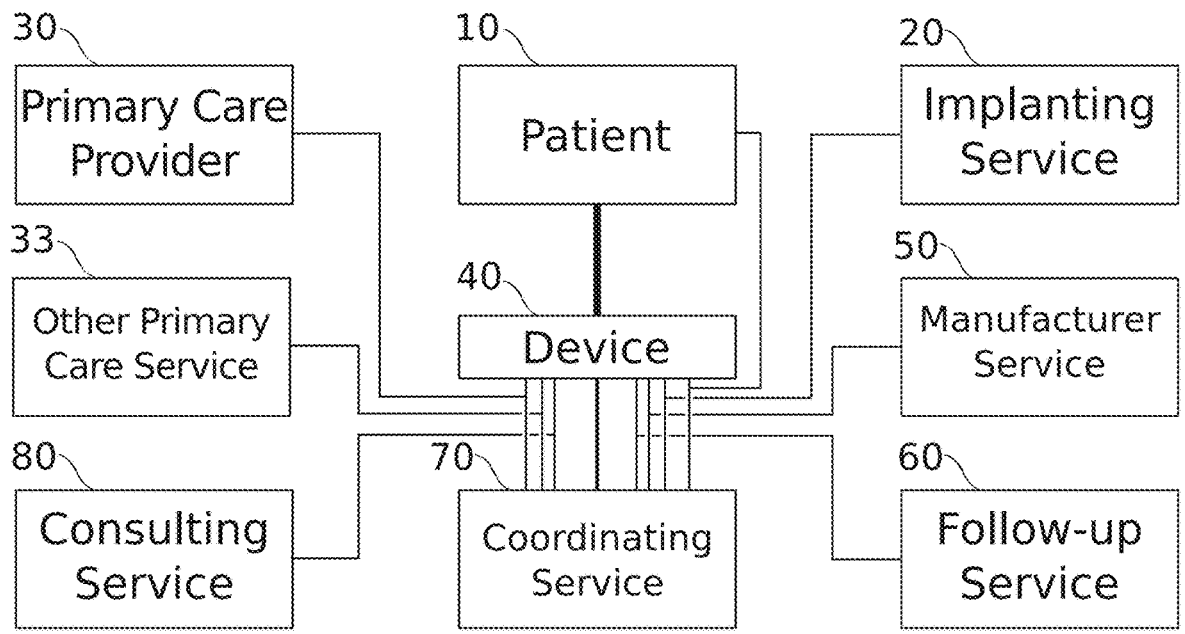
FIG. 1C schematically represents the relationship of healthcare and other services relative to a patient and a device, according to some exemplary embodiments of the invention.

Reference is now made to FIG. 1C, which schematically represents the relationship of healthcare and other services relative to a patient 10 and a device 40, according to some exemplary embodiments of the invention.

In some embodiments, tasks relating to an implanted medical device 40 are shared among a plurality of healthcare and other service providers. In some to embodiments, a coordinating service 70 mediates between these providers and the device 40.

A coordinating service 70 optionally comprises, for example, a computer server and/or a call center. Optionally, a concern of the coordinating service 70 includes ensuring that the plurality of service providers that can affect device operation do not provide conflicting operation of the device. Other optional functions of the coordinating service 70 include collecting, storing, and/or distributing configuration and/or log data about the device 40. In some embodiments, access to the device 40 is directly or indirectly through the coordinating service. Optionally, the coordinating service 70 links directly to the implantable medical device (optionally using a secure standard networking method such as wireless networking).

Optionally, controllers operate through this direct network link. Potentially this allows the coordinating service 70 to be fully aware of all activities relating to the device. Additionally or alternatively, the coordinating service "introduces" a controller to a device, for example by an exchange of tokens such as access keys.

Optional relationships between coordinating service 70, device 40, and another service include the following examples.

In some embodiments, an implanting service 20 introduces a device 40 into a coordinating service 70. Optionally, the implanting service 20 stores additional data about the device 40 on the coordinating service. For example, test and/or configuration data (optionally, alternative configuration parameter data sets) are uploaded to the coordinating service.

In some embodiments, at least a portion of the range of configuration options which will be available to a primary care physician 30 is determined by the implanting service 20, and optionally made available through the coordinating service.

In some embodiments, a primary care provider 30 interacts with a coordinating service 70 for one or more of gaining access to the implanted device 40, accessing alternative parameter sets previously configured for used with the device 40, uploading log data from the device 40, and/or communicating with other services about the device (for example, communicating with services of the implanter 20, the manufacturer service 50, and/or a consulting service 80). Optionally, a primary care provider interacts with a coordinating service 70 as part of an initial referral of a patient 10. Optionally, this associates the primary care provider 30 with the patient and device 40, for purposes such as assigning the primary care provider for care management during later treatment with the device 40.

In some embodiments, other primary care providers 33 potentially interact with the coordinating service 70 and device 40. For example, if a patient is away from the usual primary care provider 30, the coordinating service allows some subset of interactions between device and other primary care provider 33. Optionally, the main primary care provider 30 is later able to be updated about such interactions via the coordinating service 30. In some embodiments, the primary care provider 30 is contacted via the coordinating service 70.

In some embodiments, other services are brought into the system over the life-cycle of the implanted medical device 40. For example, contact with a medical consultant 80 such as a device specialist is made through the coordinating service 70.

Similarly, access to a follow-up service 60 (optionally the device implanter) is optionally arranged through a coordinating service 70. In some embodiments, a manufacturer service 50 is brought into the system, for example during operations by the implanting service 20, and/or for servicing of the device during the device life-cycle.

It is to be understood that each of these services optionally interacts with the device away from a designated coordinating service 70, and/or that there is more than one coordinating service 70, each of which coordinates a different aspect of interactions over the device 40. However, it is a potential advantage to have a single coordinating service which centralizes interactions with the device 70, for example to help ensure consistent performance tracking and device management.

Figure 1D:
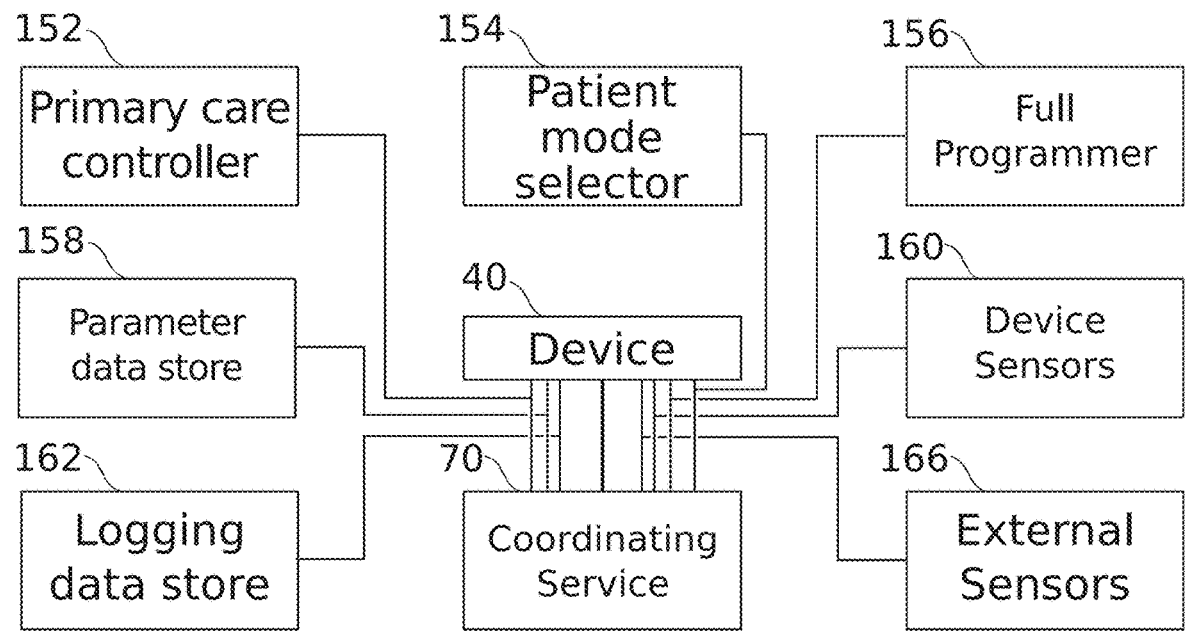
FIG. 1D schematically represents the relationship of controllers, sensors, and other components of a system supporting management of an implantable medical device, according to some exemplary embodiments of the invention.

Reference is now made to FIG. 1D, which schematically represents the relationship of controllers, sensors, and other components of a system supporting management of an implantable medical device 40, according to some exemplary embodiments of the invention.

In some embodiments, there are a plurality of different components of a medical device system which interact (directly, or indirectly, for example, through a coordinating service 70) with the implanted device 40 itself.

Some components comprise controllers. For example, a device specialist is optionally provided with a full programming controller 156, to allow programming of every available aspect of a device's operation. A primary care provider optionally uses a primary care controller 152. A primary care controller optionally provides functionality which is targeted at the tasks of primary care—for example, by presenting a reduced number of configuration options, and/or by presenting configuration options in terms of more basic clinical concepts (for example, patient performance and/or treatment regime or "dose"). A patient is optionally provided with a mode selector 154, for example, to allow control that adjusts device operation according to the patient's daily routine. It is to be understood that the physical partitioning of a controller's functions is optionally divided among device 40, coordinating service 70, and one or more additional controllers. For example, a "controller" optionally is designated by possession of a key providing access to an interface of the coordinating service 70, which is what direction accesses the implanted device 40 itself.

Some components comprise sensors. Device sensors 160 are optionally part of the device itself (provided for logging and/or to modulate device function).

Additionally or alternatively, an implanted device is configured to interact with one or more external sensors 166. These are optionally sensors of other implanted devices.

Optionally external sensing comprises information obtained from a public or semi-public source, for example, weather data, emergency services status information, or information available from a social media data source.

Some components comprise other data. In some embodiments, a parameter data store 158 is provided which stores one or more (typically, a plurality or multiplicity) valid configurations of an implanted medical device 40. Optionally, the parameter data store is part of the implanted device 40 itself. However, the parameter store is optionally part of a controller, part of and/or accessed through a coordinating service 70, and/or is a separate component. In some embodiments, a logging data store 162 is provided. The logging data store optionally stores data from the device, for example, telemetry recording operation of the device itself, and/or sensor data.

Device Parameter Changing Scenarios and Operations

Figure 2A:
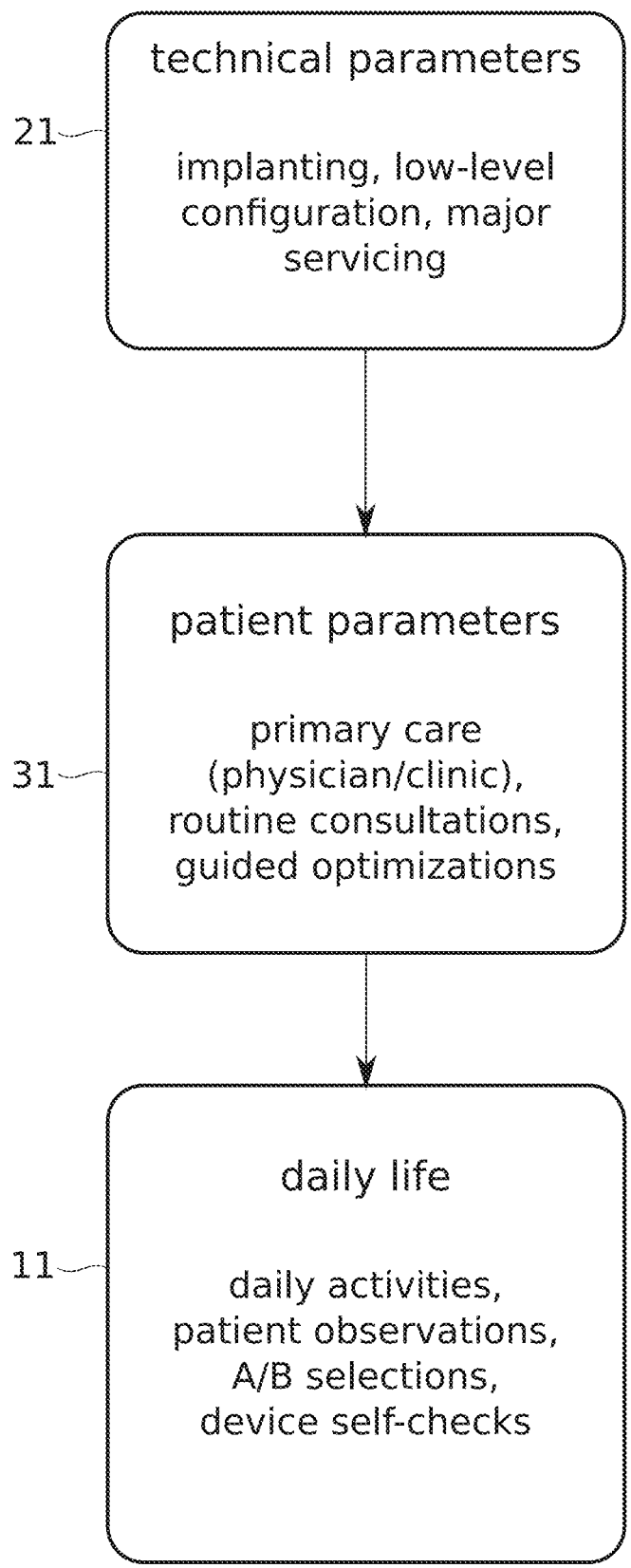
FIG. 2A is a schematic flowchart representing different domains for implantable medical device management, according to some exemplary embodiments of the invention.

Reference is now made to FIG. 2A, which is a schematic flowchart representing different domains for implantable medical device management, according to some exemplary embodiments of the invention.

In some embodiments, there are at least three domains within which an implanted medical device is operated: a technical parameter domain 21, a patient parameter domain 31, and a daily life domain 11. Roughly, these correspond to operations performed by a device implanter 20 or another device specialist, a primary care provider 30, and the patient 10 him- or herself.

In some embodiments, the technical parameter domain 21 comprises device operations where a deep level of device adjustment is potentially performed. For example, these adjustments are made together with implanting, as part of low-level post-implantation configuration, and/or as part of major servicing operations during the later life-cycle of the implanted device.

In some embodiments, patient parameter domain 31 includes management of the device in connection with primary care by a physician or clinic. Optionally, the adjustments are made at the level of managing patient parameters such as therapeutic effect and/or side-effect strength. In some embodiments, this management comprises selecting a predefined parameter set which is associated with a desired clinical effect (or change in clinical effects). Management optionally comprises deliberately introduced variations in device operation to try to optimize performance, and/or changes made in consultation between a primary care provider and a device specialist.

In some embodiments, daily life parameter domain 11 comprises functions such as functional monitoring and/or device-self checks only. Optionally, a minimal control is provided to the patient, for example, to control activation of the device with respect to patient activities (for example, to activate GCM before eating).

Optionally, a patient is allowed to select from among two or more reasonable to parameter sets, for example, in order to determine which parameter set gives results which work best with the daily routine of the patient.

Figure 2B:
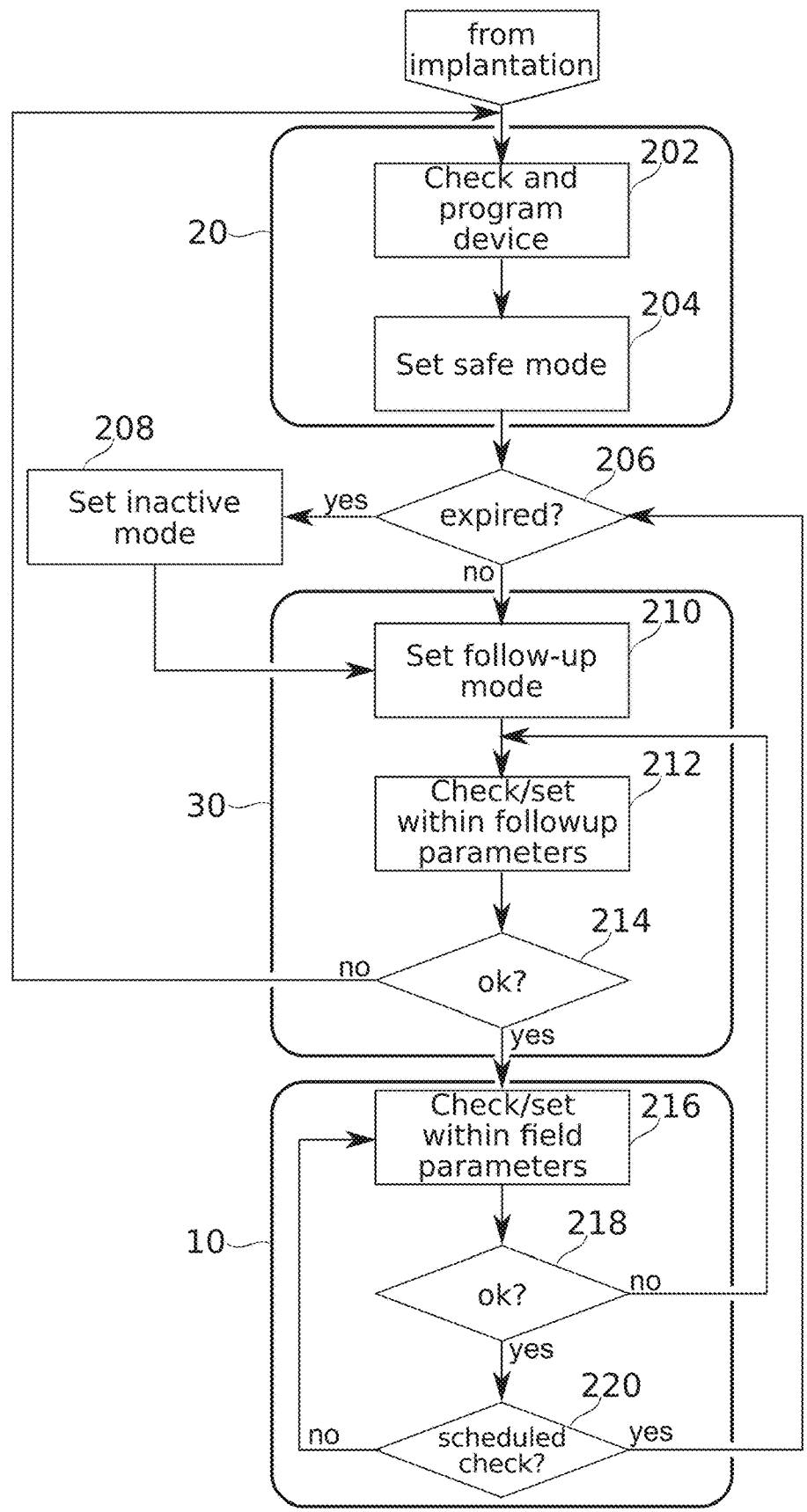
FIG. 2B is a schematic flowchart representing modes and operations of an implantable medical device, with respect to an implanting physician and/or clinic, a primary care physician and/or clinic, and a patient, according to some exemplary embodiments of the invention.

Reference is now made to FIG. 2B, which is a schematic flowchart representing modes and operations of an implantable medical device, with respect to an implanting physician and/or clinic 20, a primary care physician and/or clinic 20, and a patient 10, according to some exemplary embodiments of the invention.

In FIG. 2B, blocks 202-220 indicating activities of implanted medical device management are shown relative to blocks indicating the patient 10, primary care provider (primary care physician, staff, clinic, or other organization 30), and implant provider (implanting physician, staff, clinic, or other organization 20) in whose domain the activities occur.

The flowchart begins after implantation of the device. At block 202, in some embodiments, the device is checked and programmed by the implant provider.

Details of the programming depend on the type and model of the medical implant device provided. Examples now given relates to a rate responsive cardiac pacemaker, but it is to be understood that these examples are indicative only, and that some embodiments of the invention cover programming of other devices, changed as necessary for the functions of the device. The descriptions may be understood to include a portion of the total range of parameters that an implanted medical device can present for programming, as an indication of the scope of parameters that are dealt with in some embodiments.

In some embodiments, a rate responsive cardiac pacemaker is programmed to change the heart rate based on detected motion (acceleration, for example) of the body. For example, a piezoelectric crystal functionally connected to the pacemaker (optionally, within it) detects acceleration. Parameters that optionally define an increased heart rate response by the pacemaker to the detected acceleration include, for example:

- A minimal amplitude of acceleration that denotes an acceleration event.
- Parameters for sub-algorithms that validate the acceleration event, optionally including but not limited to: major frequency component, minor frequency component, and/or frequency modulation.
- The acceleration event durations that define each case for which a different device response is available.
- The trend of the acceleration signal as it relates to device response; for example: percentage rate of rise of the acceleration signal, percentage change within a rolling sampling window and/or the duration of that window.
- Parameters governing the response to acceleration of the pacemaker for each distinguished acceleration event case, for example: latency from acceleration case to response, rate of pacing increase, maximal heart rate, rate of pacing increase as a function of event features (for example, acceleration), and/or maximal heart rate as a function of event features.

These samples of device parameter complexity indicate the complexity of the whole device, as well as indicating the potential interdependence of parameters to be configured.

In some embodiments, parameters are set up based on testing of the implanted device and/or the patient, for example, within the clinical facilities of the implant provider. Optionally, these data are used by the implant provider to generate a default configuration (device parameter set) for the device. In some embodiments, more than one device parameter set is generated for the device, for example, based on measurements and calibrations during different activity levels of the patient in testing, based on experience with other patients, based on expected potential disease states of the patient as the disease changes over time, and/or based on known or potential effects of auxiliary medical treatments.

Although patient performance is optionally gathered during this setup stage, there are practical limits on how much data can be gathered, and furthermore, predictions of the future evolution of patient performance and/or disease state are only estimates. Even where a suitable parameter set is available for a change in conditions, the device may not be able to automatically determine which parameter set that is. For these and/or other reasons as described herein, programming and parameter set selection is optionally modified throughout the use of the implanted to medical device.

At block 204, in some embodiments, the device is optionally set into a "safe mode". The safe mode is an option whereby the device is set so that critical life-supporting functions work, while other treatment functions are inactive, and/or persist only for a limited period of time. This is a potential benefit to ensure that a patient is not subjected to a long period of unsupervised treatment after finishing initial device configuration. After block 204, the patient and the implanted medical device leave the care of the implant provider 20.

At block 206, in some embodiments, an expiration check is made on the current operating mode of the device (which may be the "safe" mode, or another mode). If the safe mode duration expires without attention from an authorized medical professional, the device optionally drops into a maximally inactive mode at block 208. Optionally, the safe mode operates for, for example, a week, two weeks, a month, three months, or another longer, shorter, or intermediate time before the inactive mode is set.

At block 210, in some embodiments, the patient enters the care of a primary care provider 30. In some embodiments, the primary care provider puts the device into a "follow-up" mode. The features of a follow-up mode can vary by device, and optionally include:

- Activation of therapeutic activities.
- Activation of device monitoring and/or recording.
- Charging of the device.
- Linkage of a primary care provider to a device (for example as described in relation to block 108).

In some embodiments, linkage of a primary care physician to a device is exclusive—that is, only one primary care provider can manage any given device. It is a potential advantage to exclusively link a primary care physician to a device, for example, to prevent accidental interference among changes made by other care providers. Nevertheless, in some embodiments, linkage of a primary care provider to a device does not preclude full access to the device by a device implanter or other device specialist.

At block 212, in some embodiments, device checks and/or updates are performed by a primary care provider. Optionally, the device is checked by a primary care provider to ensure that the device is working within expected parameters.

Optionally the performance states of the patient and the device are checked and/or considered to determine if the current set of device operating parameters should be altered. Examples of reasons to change parameter sets include a change in patient performance, a complaint by or observation of the patient, a change in the activity of the patient, and/or a change in parallel treatments provided to a patient.

In some embodiments, device configuration changes are made based on information that is unavailable or difficult to obtain at the time of initial configuration. For example, determination of a preferred device setting is dependent on patient choice—but the patient lacks experience to decide what to choose until leaving the initial care of the implant provider. Additionally or alternatively, the preferred setting is dependent on the current routine or lifestyle of the patient, and subject to change according to the patient's activities. Additionally or alternatively, the preferred setting is chosen according to medical performance data obtained over an extended period of time (months or years, for example), and/or a medical state of the patient that itself changes over time (for example, as patient well-being increases or deteriorates).

In some embodiments, a change in parameters comprises switching the device to use a parameter set that was determined (and optionally programmed into the device) at the time of initial device implantation, or predetermined at a later time.

In some embodiments, new parameter sets are provided as a range of graded (or otherwise ordered in terms of values and/or effect) changes to one or more parameters of the device. Optionally, the decision to change from one setting to the next comprises moving in one direction or the other in the parameter set order.

Optionally, details of the device parameter space is transparent to the primary care physician, and the ordering is in another parameter space, for example, a measure of patient performance, side-effect occurrence, "dose" strength, or another description of parameter state.

In some embodiments, a primary care provider guides and/or monitors "A-B" type optimizations of device parameters. For example, a primary care provider selects two or more parameter sets (from among a plurality predefined, for example, at the time of device implantation), and switches between them during different patient visits (or according to another schedule), gives the patient the freedom to choose one or the other parameter set, or otherwise arranges for real-world comparative testing. Optionally, choice is randomized, but recorded by the device for later review, allowing a blind or double-blind study at the level of an individual patient's treatment. Optionally, for example, after the results of several weeks or months of experience with the device are obtained, an implant specialist is consulted (for example, together with the primary care provider), presenting this data for further evaluation. Optionally, the device specialist uses the results to generate new parameter sets suitable for evaluation by the patient and the primary care physician.

Optionally, the primary care physician works with the patient to determine what optimizations are most desired, and the device specialist arranges new parameter sets for trial accordingly.

From block 214, in some embodiments, if the device is functioning properly and does not need reprogramming, the flowchart continues with block 216; otherwise flow optionally returns to block 202 so that the device can be serviced and/or reprogrammed.

In some embodiments, at least some types of interactions between an implanted device and the device specialist 20 are optionally mediated by the primary care provider 30.

For example, conferencing (for example, teleconferencing) or other communication is arranged between primary care provider, device specialist, and optionally the patient. In some embodiments, an implanted device and/or a support system for the device comprises facilities for remote transmission of telemetry and/or remote updating of device parameters. The primary care physician potentially plays a central role in facilitating the interaction between device specialist, patient, and device; translating the global clinical situation of the patient into subjects that the device specialist can address, and verifying, conversely, that the device specialist's solutions are consistent with the patient's clinical situation.

Blocks 216, 218, and 220 optionally occur in the domain of the patient's daily life with the implanted medical device.

At block 216, in some embodiments, device self-checks periodically occur, including verification of the status and operation of the device itself, and optionally verification that any clinical situation it has been "told" about during device configuration remains within anticipated parameters. Self-checks optionally occur continuously or with high frequency (with every pulse, for example), hourly, daily, weekly, monthly, or at another longer, shorter, or intermediate interval. Optionally, different self-checks occur with different frequencies.

In some embodiments, a patient is optionally provided with a certain amount of control over operation and/or settings of the device, for example as described in relation to block 212. In some embodiments, the patient optionally selects from among one or more available device parameter sets that have been previously cleared by the primary physician for personalized testing. In some embodiments, parameter sets are selected by the patient as part of daily use of the device— for example, to activate, deactivate, or modulate stimulation or other device activity according to the activities of the patient. Optionally, device logging records these setting changes and/or their results, providing an objective record of implanted device function that a primary physician can refer to in discussions with the patient on future visits.

At block 218, in some embodiments, if some sufficiently serious problem with device operation is found or suspected based on device checks, the patient returns to the primary care physician at block 212, so that the problem can be solved by the primary care physician and/or a device specialist if referral or consultation is found appropriate.

Otherwise, flow continues at block 220, in some embodiments. Optionally, the device determines if it is time for a scheduled check, for example, due to the expiration, completion, and/or other termination of a treatment regime. A treatment regime terminates, for example, after a certain number of uses, and/or due to achievement of a predetermined end point. Optionally, reaching the end point is automatically sensed by the device. For CCM, for example, the end point is reached according to one or more criteria of sensed acceleration, contractility, and/or heart rate. Additionally or alternatively, another criterion is set, for example, based on sensed levels of a secretion and/or blood glucose (potentially relevant, for example, to GCM in diabetics). Optionally, this results in an alert to the patient. Optionally, for example if the device has not interacted with a primary care physician recently enough to ensure continued safe operation of the device, the flowchart returns to block 206, and the device optionally enters an at least partially inactive mode at block 208 until reactivated by a primary care physician. If there is no issue requiring professional medical attention, the diagram cycles back to block 216.

Figure 3:
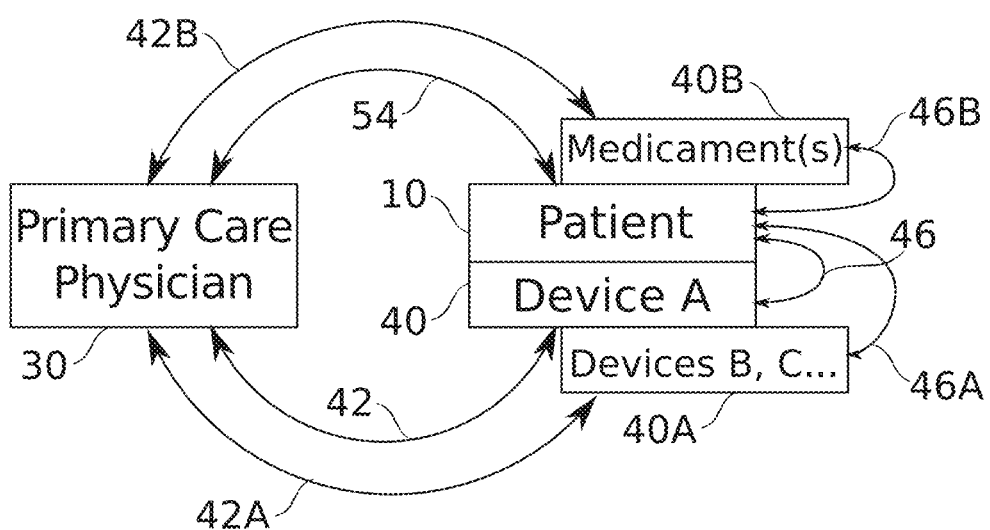
FIG. 3 is a schematic diagram representing interactions among a primary care physician and/or clinic, a patient, a first implanted medical device, one or more additional devices, and medicaments, according to some exemplary embodiments of the invention.

Reference is now made to FIG. 3, which is a schematic diagram representing interactions among a primary care physician and/or clinic 30, a patient 10, a first implanted medical device 40, one or more additional devices 40A, and medicaments 40B, according to some exemplary embodiments of the invention.

In some embodiments, a primary care physician 30 who is overseeing administration to a patient 10 of auxiliary treatment(s), for example, other devices 40A, and/or medicaments 40B in parallel with treatment delivered by implanted medical device 40 provides the device via interactions 42 (for example, programming, data entry, and/or option selection) with information about the auxiliary treatment(s) 40A, 40B. Optionally, the parameters of device 40 are altered in compensation. This is a potential advantage when there are potential interactions among the effects 46, 46B, 46A that implanted medical device 40, other devices 40A, and/or medicaments 40B have on the patient 10. Primary care physician 30 is potentially assisted in the overall goal of patient health management by this; for example, more options are potentially available for prescriptions 42B, 42A of medicaments 40B and/or management of other devices 42A, when at least one device 40 is capable of reactive changes in response to other treatments.

As an example of a situation where treatment interactions potentially arise: a patient being treated for congestive heart failure is provided with both beta blocker medicament 40B and an implanted medical device 40 for administration of cardiac contractility modulation (CCM). CCM is a treatment modality (used, for example, in the treatment of heart failure) in which electrical stimulation is applied to cardiac muscle during its absolute refractory period. Potentially, this enhances the heart's natural contractions. Potentially, CCM at least partially reverses disease-related changes to heart structure.

Optionally, the receipt and/or effect of beta blockers by the patient changes over time, for example due to changes in the prescription, changes in physiological response to a prescription, and/or changes or inconsistency in patient compliance. Potentially, these changes affect the optimal treatment parameters for CCM— for example, preferred stimulus strengths and/or timings, expected patient performance ranges, and/or threshold values.

In some embodiments, an input from a primary care physician to a CCM treatment device (or another device 40 according to an embodiment of the current invention) comprises a description of auxiliary treatments 40B, 40A. For example, the input conveys details of:

A prescription (for example, of a drug 40B or other device 40A, of dose, frequency, and/or another prescription parameter);

A patient's observed physiological responsiveness and/or compliance; and/or

Other information about the historical, current, and/or predicted course of the auxiliary treatment.

Optionally, the device is configured to operate according to device parameters that are modified based on this information. Optionally, this configuration is without directly providing information about auxiliary treatments to implanted device 40.

In some embodiments, changes in operation include activation of device features specific to operation in concert with an auxiliary therapy. For example, an implanted medical device for a heart optionally monitors the heart rate, and based on this infers whether a beta blocker prescription that it has been informed of is currently in effect or not. This potentially allows the device to dynamically change operation based on the most likely medical current physiological state of a patient.

Optionally, sensing that the device provides (for example, in order to direct its own functioning), acts as monitoring for the effects of auxiliary treatments.

Device Access Keys, Usage, and/or Management

Figure 4:
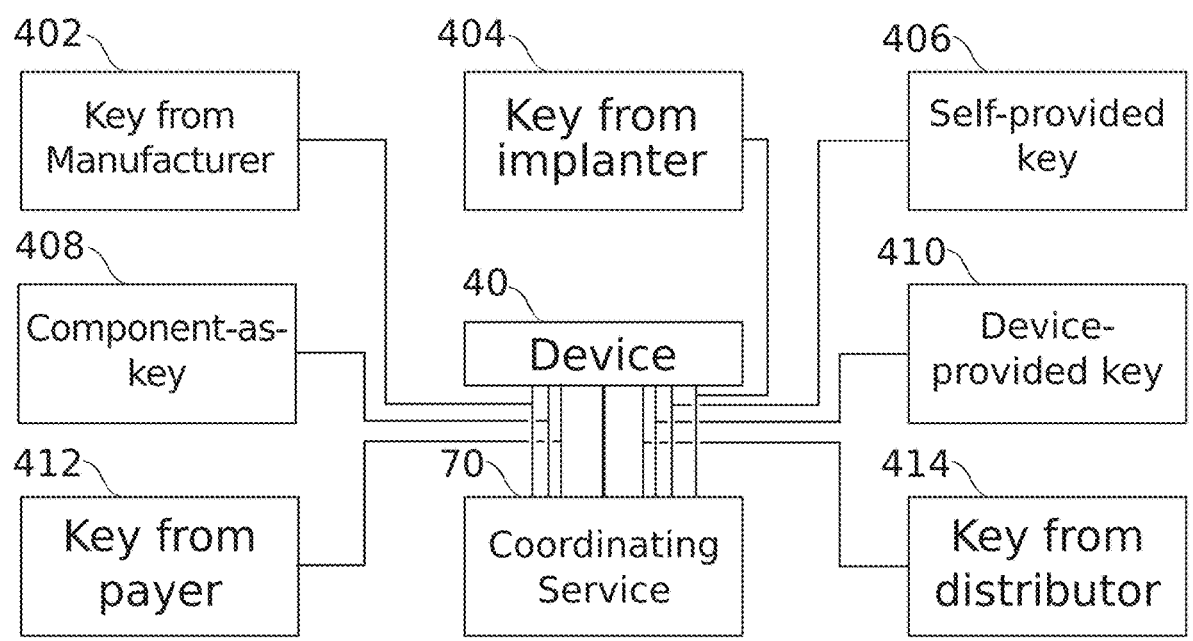
FIG. 4 schematically represents the relationship of different access key types to an implantable medical device and/or a coordinating service, according to some exemplary embodiments of the invention.

Reference is now made to FIG. 4, which schematically represents the relationship of different access key types to an implantable medical device 40 and/or a coordinating service 70, according to some exemplary embodiments of the invention.

In some embodiments, any service which interacts with a device (for example, one of the services described in relation to FIG. 1C, or another service such as an insurer, HMO, or other payer service) is optionally given access through a key. A key unlocks (or adds) one or more device functions, selected according to the configuration of the device and/or the key. The key is, for example, a number, alphanumeric string, or physical device. Validation of the key is optionally through the device 40 itself, through a controller configured to interface with the device, and/or through a coordinating service 70. FIG. 4 shows a variety of different keys according to their source and/or type, in relation to a device 40 and/or a coordinating service 70. It is to be understood that a plurality of keys optionally operate together to grant access to a device or device function. For example, a key that grants access to a particular device optionally operates together with a key that unlocks a particular therapeutic paradigm. This is a potential advantage to allow, for example, purchasing of services on an open market, while still enforcing exclusive access control over individual devices.

In some embodiments, a key 402 is provided by a manufacturer to a service provider, or a distributor key 414 is provided to a service provider.

Optionally, the key is for a specific individual device 40. Optionally, the key grants more general access: for example, to a particular device model, or for a particular range of serial numbers within the model. This access model is potentially appropriate, for example, as part of a manufacturer's certification and/or authorization of a third party service provider. In some embodiments, a distributor distributes devices and one or more distributor keys 414 separately. For example, keys which activate a therapy regime of a device 40 are distributed separately from the device itself.

In some embodiments, a key 404 is provided by an implanter or other device specialist to another service provider; for example, to a primary care physician. This is of potential benefit, for example, to create an authenticated link among service providers who will need to work together over the lifetime of a device 40, e.g., the implanted device.

In some embodiments, a key 406 is self-provided. This allows, for example, an authorized primary care provider to "sign in" to a device worn by a patient entering his or her clinic. Additionally or alternatively, a self-provided key is placed on a device by someone else. For example, a referring physician includes a key with the referral, and the implanter and/or device configurer activates the implanted device to recognize that key. Additionally or alternatively, a key 410 is provided by a device, for example, upon receiving a query requesting one. Optionally, exclusive access to a device is enforce, for example, by only issuing one such key, and/or by issuing a device-specific key only upon presentation of a key credential which allows general permission to access such a device.

In some embodiments, a key 408 is a component needed for an aspect of device operation. The source is optionally dependent on the aspect. For example, a manufacturer or distributor distributes keys which comprise a power supply for an implanted medical device, and possession of such a power supply is controlled so that it is a form of access device which allows enabling of one or more functions of the device. Additionally or alternatively, configuration data that directly enable a particular function of a device 40 are generated by a device implanter and/or configurer, but not put on the device 40 itself. Then the configuration data can only be used to enable functionality by another service provider who receives that data.

In some embodiments, a key 412 is provided by a payer, for example, an insurer or HMO. This is a potential advantage, for example, to allow marketing and sales effort by a manufacturer or distributor to be concentrated at the level of a payer organization. The payer optionally purchases keys in bulk, for example, keys which enable a therapy provided by the device, which authenticate payment for a consultation or follow-up service, or which simply serve as an identifier of a service provider for the payer.

Components of an Implantable Medical Device System

Figure 5:
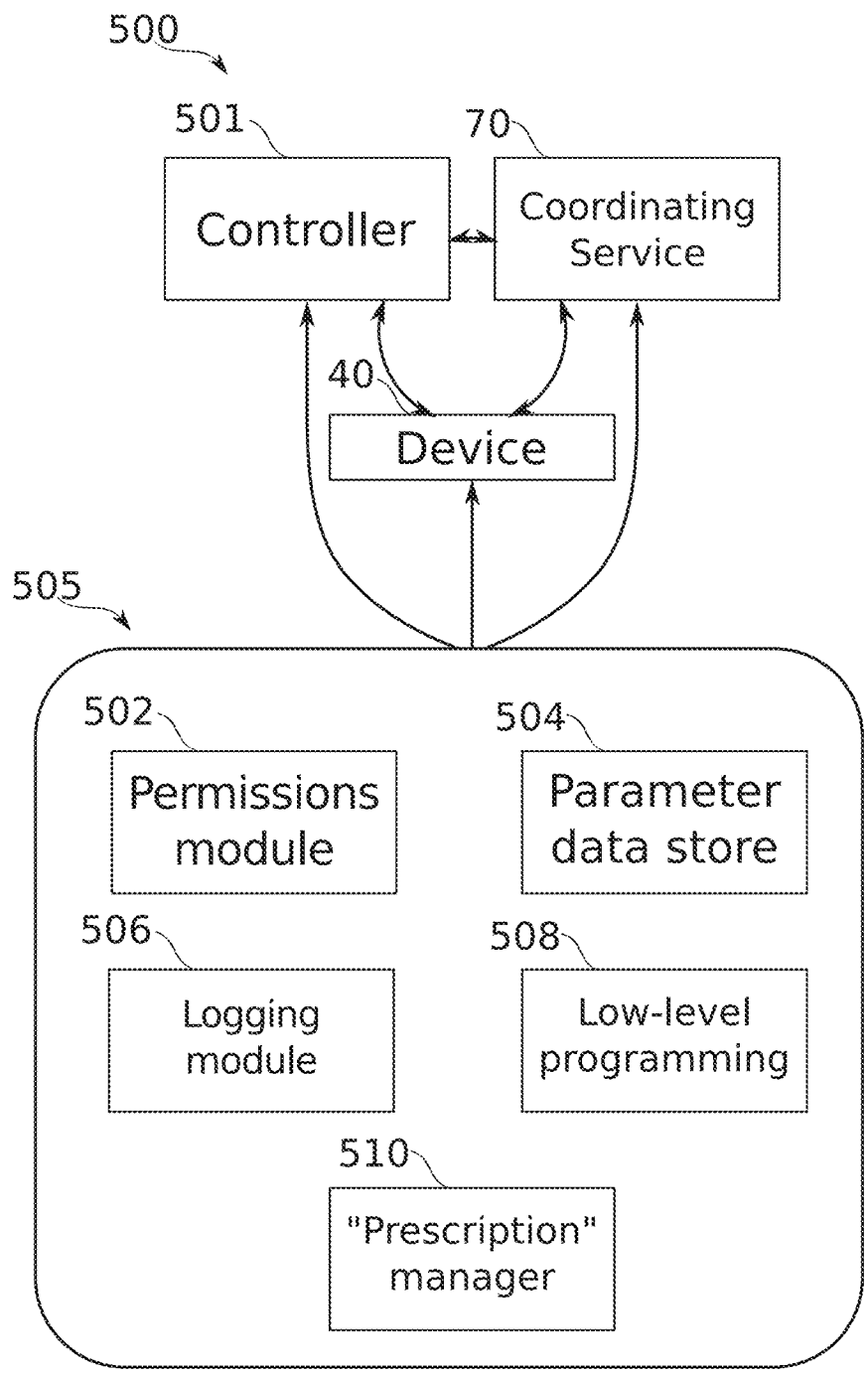
FIG. 5 schematically represents relationship among components of an implantable medical device system, from both the perspective of functional modules, and from the perspective of system components implementing the functional modules, according to some exemplary embodiments of the invention.

Reference is now made to FIG. 5, which schematically represents relationship among components of an implantable medical device system, from both the perspective of functional modules 505, and from the perspective of system components 500 implementing the functional modules 505, according to some exemplary embodiments of the invention.

In some embodiments, the main components 500 of an implantable medical device system comprise the implanted device 40 itself, one or more controllers and/or access devices 501, and optionally a coordinating service 70.

In some embodiments, the controllers and/or access devices 501 comprise one or more of the devices described, for example, in relation to FIG. 1D.

In some embodiments, the coordinating service 70 comprises a computerized server and/or call center, for example as described in relation to the coordinating services of FIGS. 1C-1D, and 4.

In some embodiments of the invention, one or more of the functional modules 505 are implemented, each by one or more of the main components 500. Particular examples include:

Permissions module 502 optionally determines which device functions can be accessed and/or modified in any given circumstances. Permissions module 502 is optionally implemented at least in part by any one or more of controller 501, coordinating service 70, and device 40. For example, access by a controller 501 to any of the functions of a device 40 upon registration, confirmation, and/or approval by a coordinating service 70. Additionally or alternatively, the device 40 and controller 501 interact directly to determine access permissions, the coordinating service unlocks the device so that the controller can function, and/or another combination of interactions is used to determine access permissions.

Parameter data store 504 optionally stores one or more parameter sets which determine how an implanted device 40 functions. The parameter sets are optionally stored on the device 40, in a controller 501, and/or provided by a coordinating service 70 (for example, received from a download server). In some embodiments, the parameter data store is initially configured by a device implanter or other specialist around the time that the device is first implanted. Optionally, the parameter data store 504 is updated during servicing, and/or by or in consultation with a device specialist, for example, in response to the requirements and/or clinical status of the patient.

Logging module 506 optionally records and/or makes available sensor data and/or device performance data. In some embodiments, an implanted device 40 comprises one or more sensors which optionally are used during normal device performance (for example, to synchronize the device to the physiology of the patient), device configuration, device diagnostics, or for another reason related to the function of the implanted medical device 40. In some embodiments, log access is directly by a readout through a controller 501, and/or mediated by a coordinating service. For example, a controller 501 mediates upload of log data read out from a device 40 to a server of the coordinating service 70, which optionally distributes the log data to medical care providers such as implanters, specialists, and/or primary care physicians, as needed.

Low-level programming module 508, in some embodiments, is used for detailed device parameter configuration. In some embodiments, a special controller (for example, programming controller 156) accesses the device for programming.

Optionally, parameters are mirrored on a server of the coordinating service 70.

Additionally or alternatively, parameters are obtained from the coordinating service 70, optionally through use of a controller 501, or otherwise after presentation of a key which is associated with the correct permissions.

Prescription manager module 510 optionally controls aspects of the operation of implanted medical device 40 from the perspective of treatment. Any or all of the system components optionally implement at least a portion of prescription manager 510. For example, a treatment plan is purchased from and/or with the verification of a coordinating service 70. Optionally, a prescription or permission token from the coordinating service 70 unlocks the ability of a controller 501 to activate a treatment to plan on a device 40. Additionally or alternatively, the controller 501 transmits an unlocking token to a device 40 to directly unlock a treatment plan.

It is to be understood that the preceding descriptions of system architecture, including the division of modules 505 among system components 500, and specifics of their interactions, are non-limiting examples indicative of how the functions of modules 505 are optionally implemented in an implanted medical device system.

Lifecycle of an Implantable Medical Device

Figure 6:
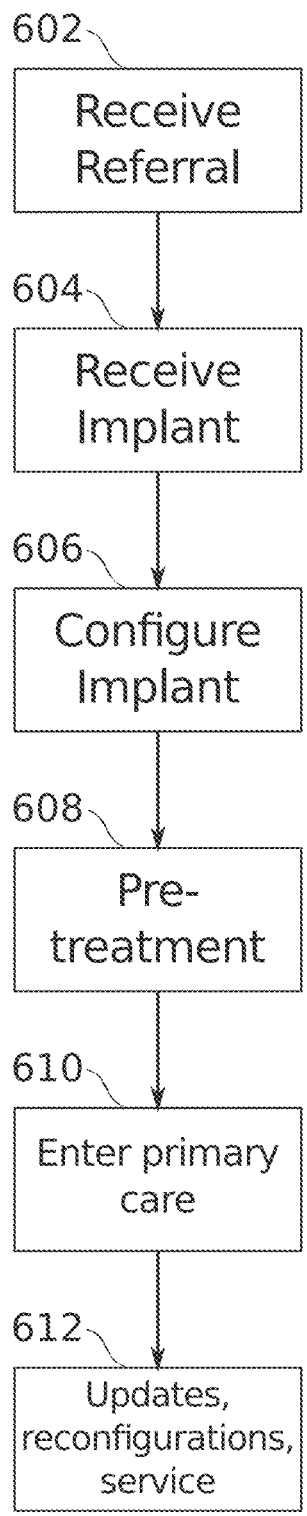
FIG. 6 is a schematic flowchart of a patient moving through the life-cycle of an implantable medical device, according to some exemplary embodiments of the invention.

Reference is now made to FIG. 6, which is a schematic flowchart of a patient moving through the life-cycle of an implantable medical device, according to some exemplary embodiments of the invention.

At block 602, in some embodiments, a patient optionally receives a referral from a primary care provider. Optionally, an arrangement is made at this time to associate the primary care provider with the implant and/or implantation process. For example, the patient is given a key identifier to bring to the device implanter.

At block 604, in some embodiments, the patient receives an implant.

At block 606, in some embodiments, the implant is configured. Optionally, the implant is configured by the device implanter, or another implant specialist. In some embodiments, configuration of the implant includes configuration of facilities (such as alternative device parameter sets, accessible ranges of parameter values, and/or other functionalities) which will later be used by a primary care provider such as a physician or clinic.

At block 608, in some embodiments, the patient is in a pre-treatment phase of implant wearing. Optionally, a device does not become fully active (for example, for the administration of an elective treatment such as CCM or GCM), until it is registered with or otherwise "unlocked" by a primary care provider.

At block 610, in some embodiments, the patient enters primary care under the supervision of a primary care provider. Optionally, this comprises unlocking access to the implanted medical device with a key possessed or obtained by the primary care provider. Optionally, the primary care provider is the same provider who gave the initial referral at block 602.

At block 612, in some embodiments, the device optionally undergoes updates, reconfigurations, and/or servicing. Optionally, a primary care provider acts as a gatekeeper to such changes. For example, the primary care provider arranges a consultation with a device specialist (optionally a remote consultation), arranges a data connection to provide log information to a device specialist, updates the device specialist on patient history and/or care requirements, or otherwise participates in device maintenance.

Patient, Device, and Medical Caregivers

Management of Device Configuration

Figure 7A:
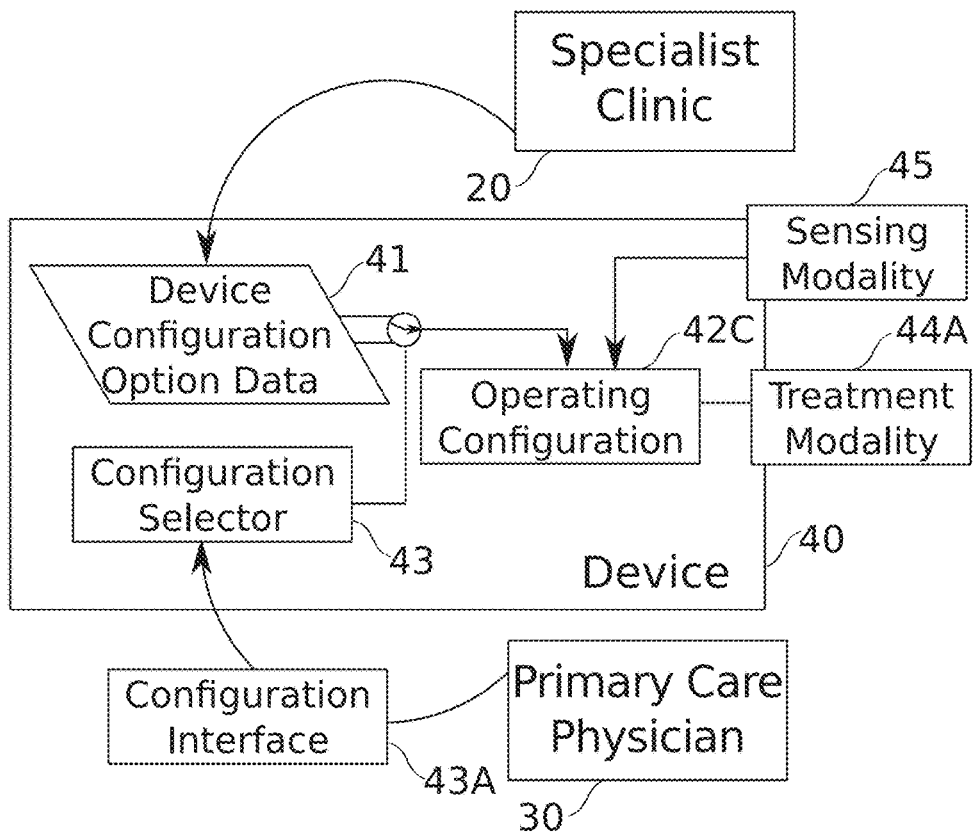
FIG. 7A is a schematic diagram of an implantable medical device which is selectably configured to produce therapeutic effects via a treatment modality over one or more physiological parameters; optionally based on patient performance sensed by a sensing modality, according to some embodiments of the present disclosure.

Reference is now made to FIG. 7A, which is a schematic diagram of an implantable medical device 40 which is selectably configured to produce therapeutic effects via a treatment modality 44A over one or more physiological parameters; optionally based on patient performance sensed by a sensing modality 45, according to some embodiments of the present disclosure.

In some embodiments of the invention, an implanted medical device 40 is configured to produce a therapeutic effect (for example, a form of physiological control) via a treatment modality 44A. The treatment modality comprises, for example, an electrical stimulator, a magnetic stimulator, supply of a pharmacologically substance, or another treatment modality appropriate to a targeted function of the implanted medical device. In some embodiments, device 40 is a device for electrically modulating heartbeat activity, such as a pacemaker.

As implanted medical devices grow in sophistication, device configuration comprises determining settings for an increasing number of device parameters.

In some embodiments, an operating configuration 42C comprises at least 10, 30, 50, 100, 150 or more configurable parameters in the technical domain which control how a device operates. In some embodiments, the parameters govern how a treatment modality 44A is activated. For example, parameters of an electrical stimulation pulse train optionally include parameters governing pulse length, duty cycle, pulse number, pulse shape, pulse-train shape (ramping frequency, for example), and/or other parameters which affect how treatment is delivered.

In some embodiments, the operating configuration 42C includes technical domain parameters governing treatment modality 44A; optionally based on inputs from a sensing modality 45. For example, sensing modality 45 optionally comprises an electrode configured to sense autonomic nervous system inputs to the heart, based on which a heart pacing treatment modality 44A induces and/or allows changing of a current heartbeat rate and/or a current heartbeat range.

In some embodiments, operating configuration 42C is selected from among options described by device configuration option data 41. Optionally, device configuration option data 41 comprise a selection of discrete configuration options available, and/or descriptions which specify one or more ranges which can be adopted by one or more variable parameters. Optionally, range specifications include constraints specified with respect to other variable parameters.

Despite the flexibility in device operation that the use of large numbers of parameters potentially provides, selectable configuration on top of this provides a potential advantage for adapting to individualized and/or dynamic performance requirements for delivery of treatment.

In some embodiments, selection of an operating configuration 42C is controlled via a configuration selector 43. In some embodiments, configuration selector 43 operates to select an operating configuration 42C from device configuration option data 41 based on measurements and/or observations of states in a patient performance domain. For purposes of explanation, the patient performance domain is conceptualized herein as a patient performance "parameter space", wherein an abstractly conceived parameter space is defined by one or more parameter-associated axes or dimensions, along or through which ordered parameter settings are defined.

It is a feature of some embodiments of the invention that a parameter in parameter space is evaluated at least according to a targeted direction of change.

Optionally, the performance parameter space is based on one or more quantified physiological parameters, such as the results of physiological testing. In some embodiments, there is further distinguished a control domain (explained in terms of a "control space") which is mapped to effects in the patient performance to domain, but with a different definition of axis direction and/or dimensionality. For example, a one-dimensional control space optionally selects control configurations which span a two-dimensional patient performance space, which in turn spans a higher-dimensional device parameter space, as will now be further explained, and also as explained, for example, in relation to FIGS. 8A-8G.

Configuration selector 43 optionally interfaces with controls for switching incrementally among operating configurations 42C; for example, switching one step in parameter space per press of a button. Preferably, the physical configuration controls are not part of the implanted portion of the device, but rather are provided as part of an external control interface 43A that communicates to the operating (e.g., implanted) portion of the device via a port, wireless communication interface (e.g., a radio link), or other communication link. It is to be understood that the interface optionally comprises any suitable arrangement of interface elements, physical or graphical, and activated by closing of contacts, control of a cursor, activation of a touch screen, or otherwise.

In some embodiments, device configuration option data 41 are provided as part of the configuration interface 43A (either additionally to or instead of within an implantable portion of the device 40 itself). Then interface 43A optionally acts substantially as a programmer for the device, except that only a limited portion of the device configuration option data are sent to and stored on the device 40 itself at any given time.

Optionally, a pair of controls is configured for up/down selection, e.g., "+" and "−" buttons with opposing effects. Optionally, more than one such pair of controls is provided, for example, to allow separate control of the selection of operating configuration 42C with respect to two or more at least partially independent treatment and/or side effects. Optionally, controlling of operating configuration 42C by configuration selector 43 comprises another form of selection, for example, selection by entry of one or more values, which index into or otherwise select from among the options defined by the device configuration option data 41. In some embodiments, configuration interface 43A provides at least one default reset command, allowing, for example, a rapid return to a last-known-good configuration, a configuration which is targeted for maximum safety (potentially at the expense of causing additional effects which are unsuitable for daily use), and/or rapid return to another configuration.

In some embodiments, the device configuration option data are established, for example, near the time of implantation, by a specialist clinic and/or physician 20.

The specialist clinic comprises the special expertise needed to define operation of the implanted medical device in terms of device operation parameters specified within the device parameter domain (optionally also associated with a device parameter space, as described, for example, in relation to FIGS. 8A-8G).

The device parameters directly specify low-level device functionality.

Optionally, the relationship between the device parameter domain and the patient performance domain can be as straightforward as the adjustment of a single parameter in the device parameter domain, mapped to a single parameter in the patient performance domain. Optionally, however, any number of patient performance parameters is mapped onto any number of device parameters.

For example, a maximum heart rate allowed by a heart pacing device is optionally mapped onto a patient performance domain comprising a measure of the patient's exercise tolerance. Control of the device by a primary care provider then optionally comprises providing the device with a command corresponding to "increase exercise tolerance", leading to a result of an increased maximum heart rate.

In a somewhat more complicated case, there are optionally other device parameter adjustments applied to compensate for secondary effects of the change in exercise tolerance. For example, parameters related to the sensing of a triggered event such as atrial fibrillation are optionally relaxed to reduce the incidence of false positives. In compensation, there may be further changes to parameter settings; for example, more aggressive ramp-up to actions taken by the device when atrial fibrillation is clearly detected. Potentially, any or all of these adjustments occur without the primary care provider needing to be aware of their details.

In some embodiments, operation of the configuration selector 43, and in to particular, ordinary operation for selection of an operating configuration 42C based on evaluation occurring in the patient performance domain, is by a primary care physician 30, and/or another non-specialist health care provider, after low-level programming has been separately provided. Herein, device operating configurations 42C and device configuration option data 41 are sometimes herein referred to as being specified in device parameter space, and/or as comprising specifications of device parameters. Herein, specification of a setting for configuration selector 43 is also referred to, for some embodiments, as comprising specification in patient performance space. The relationship between device parameter space and patient performance space is also described, for example, in relation to FIGS. 8A-8E herein.

Figure 7B:
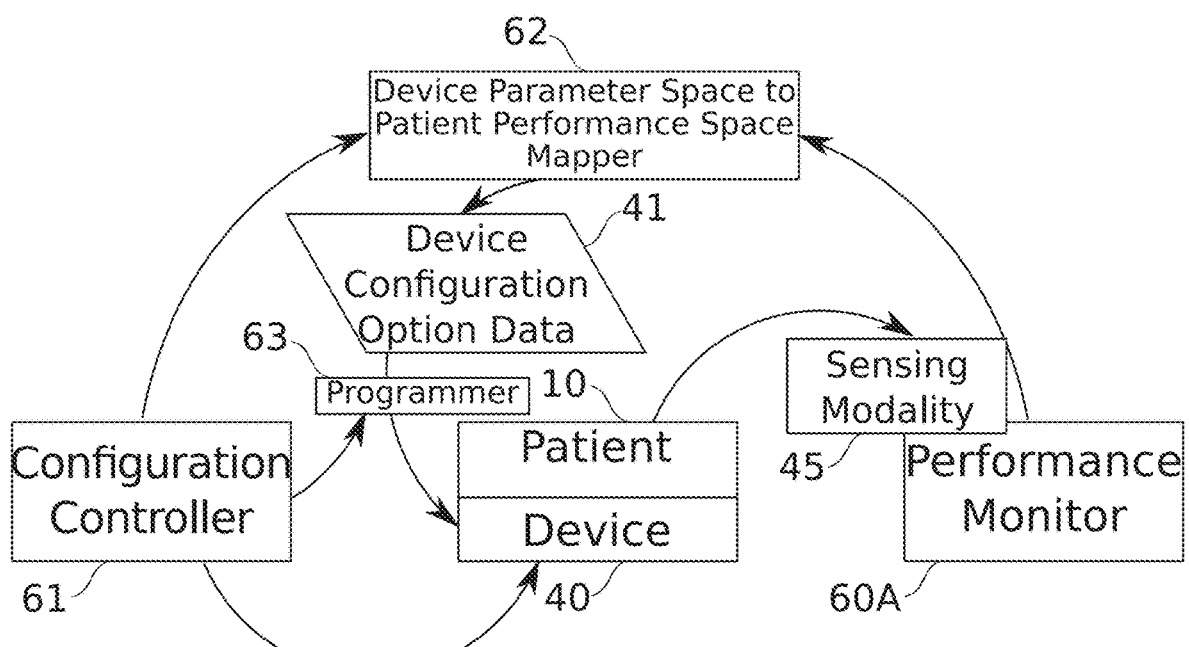
FIG. 7B is a schematic diagram of a system for configuring the device configuration option data of an implanted medical device, according to some exemplary embodiments of the present disclosure.

Reference is now made to FIG. 7B, which is a schematic diagram of a system for configuring the device configuration option data 41 of an implanted medical device 40, according to some exemplary embodiments of the present disclosure.

In some embodiments, device configuration option data 41 are programmed into an implanted medical device 40 by a device programmer 63, optionally by operation of an associated user interface for programming the device. In some embodiments (for example, where some or all of device configuration option data 41 resides with a configuration interface 43A before being selected from and send to a device 42C), device programmer 63 optionally passes the device configuration option data 41 to configuration interface 43A, which in turn provided it to device 40.

Optionally, device programmer 63 is itself part of the configuration interface 43A. Physical separation of storage of the device configuration option data 41 from the implanted portions of the device 40 provides the potential advantage of decoupling activities such as updates and other servicing from requiring the physical presence of the patient. Optionally, it can also help ensure and/or verify that configuration changes are provided only at well-defined times such as when interface 43A and device 40 are in communication. Storage of device configuration option data 41 on the implantable portion of the device 40 provides a potential advantage, for example, insofar as the configuration data are available for automated self-checks. Closer physical association to the patient also ensures presence and/or identity of the configuration data, which is a potential advantage, for example, in an emergency condition.

Optionally, device configuration option data 41 comprise descriptions of test configurations, used in the calibration of an implanted medical device 40. Optionally, device configuration option data 41 comprise data generated by a device parameter space to patient performance space mapper 62 (mapper 62). The data are generated, for example, based on correlations determined by mapper 62 between settings selected on the device (for example, by a configuration controller 61), and resulting effects on patient 10 in patient performance space measured, for example, by performance monitor 60A (optionally via one or more sensing modalities 45).

Configuration controller 61 optionally operates to set operating configuration 42C by means of selections passed to configuration selector 43, via control of programmer 63, and/or optionally operates via a separate dedicated input channel.

Arrangements are such that mapper 62 is able to match different operating configurations 42C of the device (in device parameter space) to corresponding results in patient performance space (as determined, for example, by performance monitor 60A). Examples of methods for configuring device configuration option data 41 are also described herein, for example, in relation to FIGS. 11A-11B, 12, and/or block 304 of FIGS. 9A-9B.

Parametric Configuration of an Implant Device

Figure 8A:
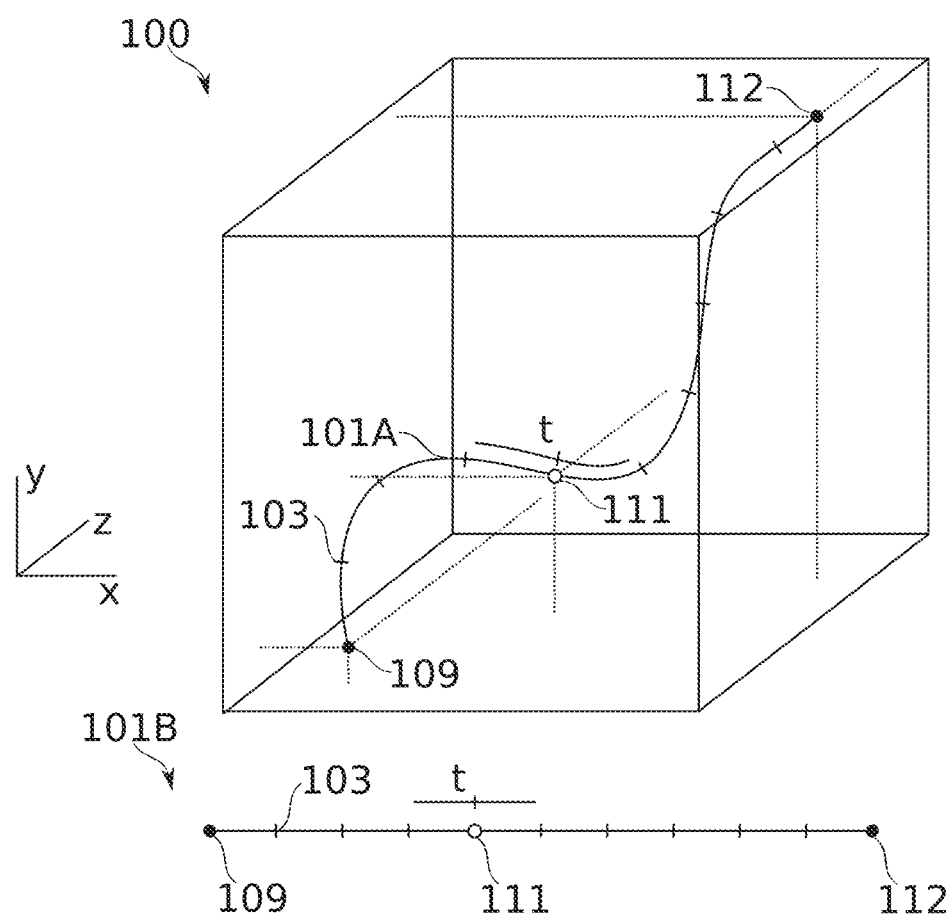
FIG. 8A schematically represents a parameter space of potential medical implant device parameter configurations, from which members of a subset of available configurations are selectable according to an ordered arrangement of the configurations along a parametric function, according to some embodiments of the present disclosure.

Reference is now made to FIG. 8A, which schematically represents a parameter space 100 of potential medical implant device parameter configurations, from which members of a subset of available configurations 109, 111, 112 are selectable, according to an ordered arrangement of the configurations 109, 111, 112 along a parametric function 101A, 101B.

In the terms described in relation to FIGS. 7A-7B, parameter space 100 optionally represents a device parameter space, while parametric function 101A, 101B optionally represents a patient performance space.

In some embodiments, an implantable medical device 40 comprises a number of configurable parameters (the number can be a hundred or more), which are programmed to govern operating characteristics of the device 40 in vivo. These configurable parameters are optionally considered as comprising corresponding components of a vector in a device parameter space 100. For purposes of illustration, three such components are represented in FIG. 8A as corresponding to x, y, and z spatial axes; however, the actual parameter space may have more dimensions (not shown). It is to be understood that the actual number of such components can be any number N, according to the number of configurable parameters.

By these conventions, each available device configuration corresponds to an N-dimensional vector indicating to a particular point in an N-dimensional parameter space 100. In FIG. 8A, the three selected components of a few such points are individually singled out as configurations 109, 111, and 112. Hash marks such as hash mark 103 correspond to a few additional such configurations. Curve 101A, shown connecting all these points, gives them an order, stretching between configuration 109 at one end of curve 101A, to configuration 112 at the other end, and passing through all the configurations 103 and 111 on the way. Curve 101A is optionally considered as a function $f(t)$ of parametric variable t. Although a continuous curve is shown for purposes of illustration, $f(t)$ is optionally only defined, for example, at discrete configurations such as 109, 111, and 112, and/or as indicated by hash marks 103.

An alternative representation of $f(t)$ is shown as the graph of line 101B. Here, the portion of patient performance space shown comprises one dimension (represented by horizontal distance). The variable t is optionally considered as corresponding to a patient performance metric, for example, a level of a treatment effect or a level of a side-effect. It is to be understood that this "level" is not necessarily quantified. However, level is preferably defined at least in terms of relative ordering; i.e., there is a progression from more to less of an effect by motion in a single direction between configuration 109 and configuration 112.

In relation to components enumerated in FIG. 7A: in some embodiments of the invention, operating configuration 42C is selected from among configurations such as configurations 109, 111, 112 lying along graph 101A, 101B. Graph 101A, 101B, representing the collection of all (currently) selectable configurations, optionally corresponds to device configuration option data 41. Optionally, a setting of configuration selector 43 is what selects operating configuration 42C from one of the selectable configurations lying along graph 101A, 101B. The configuration of the device is optionally considered as being parametric, insofar as the selection of device parameter settings is defined to be dependent on a selection of the parameters of a target patient performance state.

Device Configuration Option Selection and Ordering

Reference is now made to FIGS. 8B-8E, which schematically represent a medical implant device parameter space 200 and some particular implant device configurations 240, 211, 242, 213, within it, together with indications of relative magnitudes of targeted treatment effects 201, 201A, 203 and/or of preferably avoided side effects 202B, 202A, within different regions of the parameter space 200, according to some embodiments of the present disclosure.

In some embodiments, configuration of an implanted medical device 40 comprises two different activities: selection and/or mapping of operating configurations (in device parameter space) to patient performance space; and governing of configuration movement through patient performance space by use of a configuration selector 43.

At each stage, there is optionally a transformation in dimensionality, potentially enabling a variety of different configuration and control scenarios. For example, control of device configuration is optionally exerted along a control axis defined with respect to two or more dimensions of patient performance space, while patient performance space itself is optionally defined within a larger dimensionality of device parameter space. The sections below include descriptions of how aspects of relatively dimensionality optionally affect mapping.

Single Patient Performance Parameter Configuration Selection

Figure 8B:
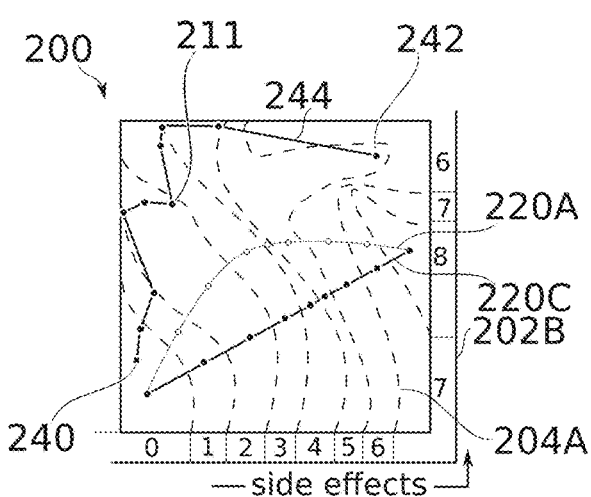
FIGS. 8B, 8C, 8D and 8E schematically represent a medical implant device parameter space and some particular implant device configurations within it, together with indications of relative magnitudes of targeted treatment effects and/or of preferably avoided side effects within different regions of the parameter space, according to some embodiments of the present disclosure.
Figure 8C:
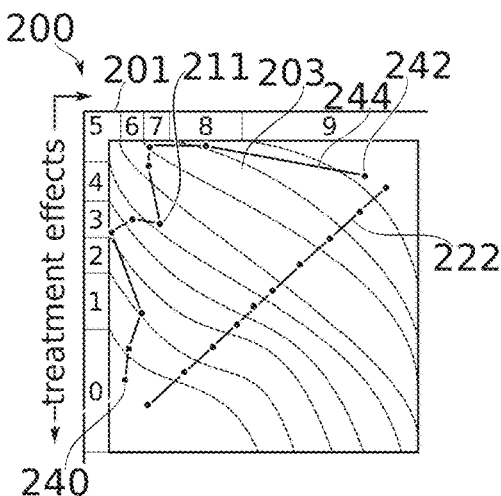

FIGS. 8B and 8C separately show isocontours representing the boundaries of regions of different relative magnitudes of side effects (contours 204A, FIG. 8B), and treatment effects (contours 203, FIG. 8C-8D) in different regions of device parameter space 200. What is explicitly shown illustrates two-dimensions of a device parameter space in x and y, overlaid with two different one-dimensional patient performance spaces defined by the isocontours.

Corresponding effects evaluation scales 202B and 201 are shown in arbitrary units, with higher numbers representing relatively stronger effects. Measurements establishing these contours relating device configurations to patient results are optionally determined at the time when an implanted device is calibrated for use, for example as described in relation to FIGS. 11A-11B herein. For purposes of explanation, effect magnitudes are shown as having discrete integral values (within each band between adjacent isocontours); however, effects are optionally continuous in value, or have "values" comprising assignment to one or more effect categories.

Treatment and/or side effects are optionally subjectively or objectively evaluated. For example, a side effect is optionally expressed as a reduction in the upper range that a heart rate is allowed to reach (objective, numeric, and optionally continuous or discrete). Optionally, a related side-effect comprises a degree of patient exhaustion associated with a task, ranked as "none", "some", "a lot", "impossible to perform" (optionally at least partially subjective, discrete, and according to category). Optionally, different effects are not inherently rank-ordered (for example, if there are two independent side effect gradients under adjustment control by a single parameter of a configuration selector 43, and/or if side effects are described as purely categorical). However, it is preferable for effects to be assigned some ordering at the time of device calibration so that adjustment of a selected device configuration can be treated as movement along a monotonic gradient (for example, a gradient of relative preference), for example as described in relation to FIG. 8A. In some embodiments, parameter changes comprising differences in two or more distinct effects are combined and ordered along one ordered listing or gradient, allow single-axis selection.

The axes (x and y) of parameter space 200 represent settings of arbitrary implant device configuration parameters. For purposes of description, two device configuration parameters (optionally, two groups of co-varying device configuration parameters) are shown; however, it should be understood that parameter space 200 optionally comprises any number of dimensions corresponding to configuration parameters suitable for the implant device. For purposes of description, parameter values are considered as continuously varying along each axis, however, it should be understood that in some embodiments the parameter settings are discreetly variable.

Turning now to the topic of control, reference is made within FIGS. 8B-8C to selectable configuration orderings 220C and 222, each of which comprises a "control space" that closely corresponds to a respective patient parameter space defined by isocontour groups 204A and 203. Such a relationship between control space and patient parameter space exists in some embodiments, for example, where concern focuses on essentially just one patient performance axis of concern (for example, optimal treatment level as such, or tolerance to a side effects level).

Configuration ordering 220C shows an set of parameter configurations covering a range of side effect levels, one configuration per level—but optionally selected arbitrarily from within that effect level (for example as shown by configuration ordering 220A). This provides a potential advantage, for example, when it is understood that increased side-effect and increased treatment effect occur in close correlation, while a target patient performance metric relates to the side effect. Reasons for targeting assessment to a side-effect (in contrast to assessment of the intended treatment effect) could include, for example, relative ease of assessment, and/or a critical requirement to keep a certain side-effect performance metric within a safe acute, chronic, and/or cumulative level.

Such a situation could arise, for example, in the case of an organ regulating device (such as a pace maker) which limits organ output (such as heart rate) to a narrow range to avoid triggering organ imbalance. From this perspective, the best treatment option is optionally "no variation" (most extreme setting); however, the side effect is to prevent normal auto-regulatory behavior in response to activity and/or environment. Then the example of range 220C (FIG. 8B), in some embodiments, optionally allows choosing from among predetermined performance range widths by providing points along an arbitrary scale of device parameter configurations, including one point at each selectable level of side effects. The ordering of the parameter configurations, optionally, is according to increasing/decreasing level of side effects. Control of configuration selection is optionally performed by stepwise movement through the ordered list of configurations available, for example as described in relation to FIG. 8A.

Alternatively, (turning now to FIG. 8C), the standpoint is optionally adopted that there is an optimal treatment level produced by a device, irrespective of side-effects (the case of "additionally" is discussed with respect to FIG. 8D, hereinbelow). Then selection of a particular device configuration optionally comprises moving up or down between treatment levels. For example, a threshold level (a maximum heart rate, for example), is preferably set for a device so that the device never allows an organ to enter a performance regime where some adverse event (such as atrial fibrillation) could occur, while keeping the operating range as large as possible. Then range 222 optionally represents device configurations providing different thresholds for this treatment effect.

Although potential reasons to choose one standpoint (treatment- or side-effect centered) or the other have been described, it can be understood from the foregoing closely related examples that the choice of standpoint is potentially arbitrary; for example, when side effects are a necessary and direct consequence of treatment effects (and/or vice versa).

Optionally, both standpoints co-exist, potentially without distinction (that is, it is simply understood that more treatment yields more side effect).

Dual Patient Performance Parameter Configuration Selection

In some embodiments, treatment effects and side effects are at least partially decoupled from one another with respect to the selection of device parameter settings. Optionally, a device according to some embodiments of the current disclosure is configured to take advantage of this decoupling in the selection of available device configurations, and/or how device configurations are ordered for controlled selection.

Figure 8D:
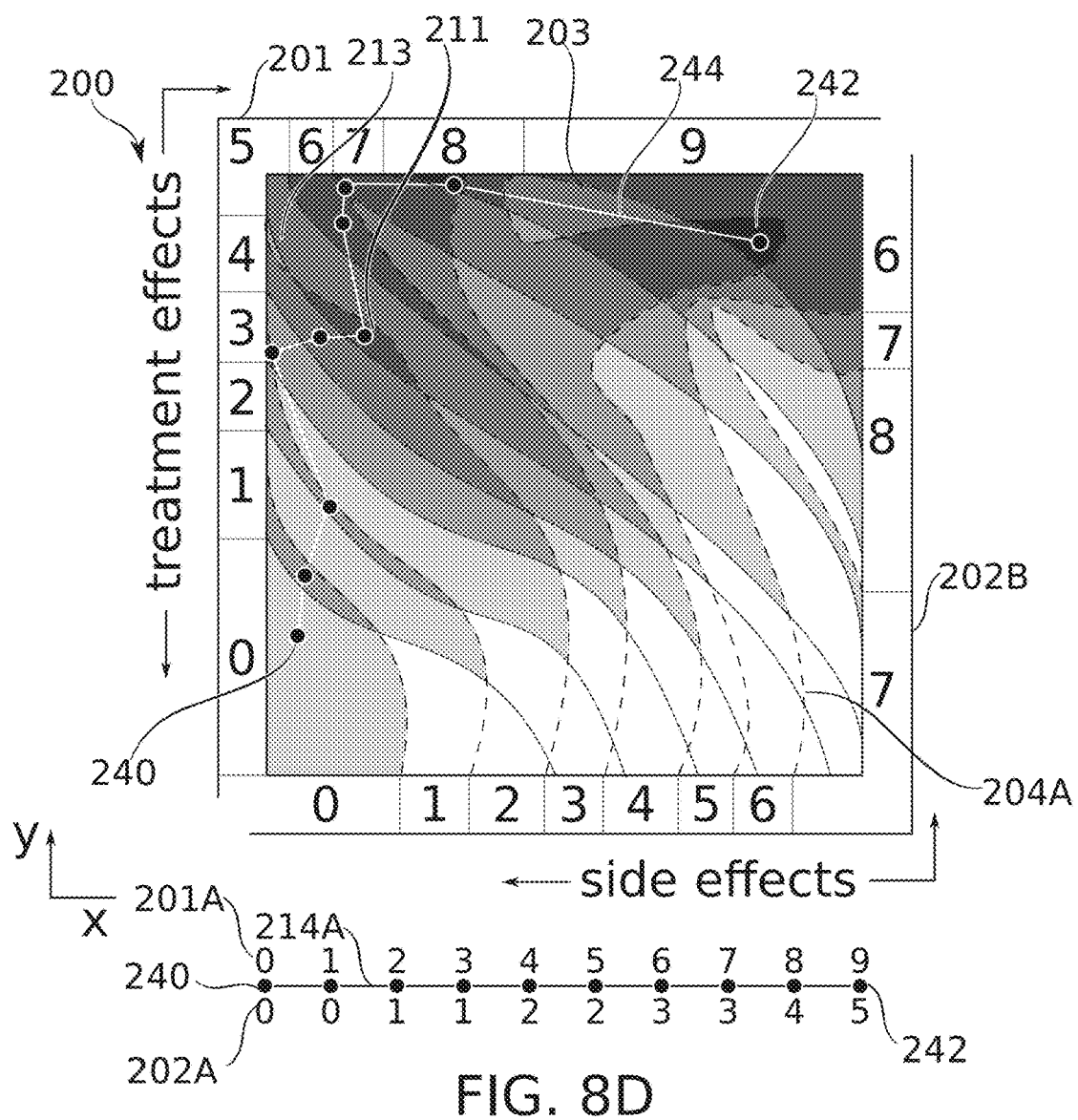

Turning now to FIG. 8D, contour groups 203, 2014A from FIGS. 8B-8C are shown overlaid, with the addition of shading to help demonstrate relationships between the two contour groups. Relatively darker shading represents relatively greater treatment obtained effects compared to side effects produced for each device configuration. For example, the first level of shading darker than white is used when both side effects and treatment effects are ranked the same (e.g., both at level 0, 1, 2, 3 . . . ). Increasingly dark shading is used as the magnitude of treatment effects rises relatively above that of corresponding side effects. Since the rankings are arbitrary, no particular significance applies to the absolute values shown. However, the pair (0,0) optionally represents no treatment applied, and thus no effects of either type.

In some embodiments, an implant device is provided with a plurality of selectable pre-defined configurations, for example, configurations 240, 211, 242, and 213. Furthermore, the configurations are ordered, as shown by segments 244 connecting the configurations.

The selection and/or ordering of configurations is optionally influenced by what will be a primary focus (but not necessarily a sole focus) of decision making in moving along a treatment spectrum in patient performance space. For example, for devices providing "best if maximal" treatment, moderated mainly by tolerance to side effects: selecting and/or rank-ordering configurations is optionally according to distinctions among side effects produced. For devices and/or situations where selecting a balance reflecting a precise treatment level is more important, it is optionally preferred to focus configuration selection and ordering on distinctions among treatment effects produced.

Furthermore, one device optionally operates within more than one regime of respective treatment- and side-effects, and criteria for controlling that operation are optionally different between these regimes. For example, one regime optionally includes how the device behaves when the patient is at rest, and another how the device behaves when the patient is active. According to a potentially shifting balance of concerns in each domain for patient performance characteristics such as safety, comfort, freedom of activity, etc., a relative emphasis on treatment effects or side effects is optionally also different in each domain.

It should be emphasized, moreover, that choice of configurations to include in a range, and the organizing of configurations in some order within that range, are distinguishable operations, optionally relying on different criteria. The first operation refers more to determining what options are available with the configured device; the second operation refers more to how the configured device options are controlled.

Considerations for each of these two operations will now be discussed in turn.

Figure 8E:
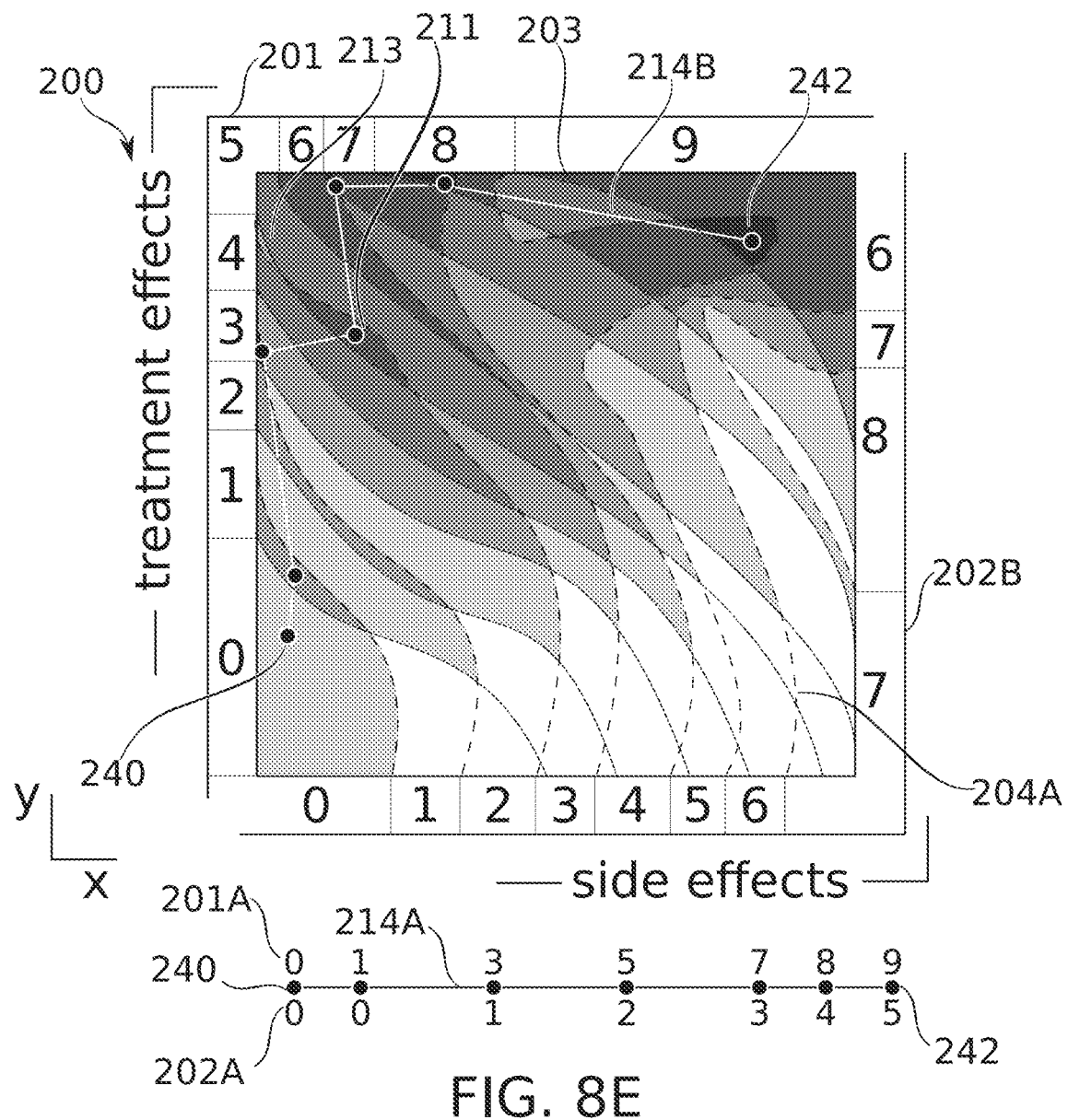

As to the choice of device configurations available for selection: in FIGS. 8B-8D, the locations of selectable device configurations in parameter space 200 (falling along path 244) are shown chosen according to a rule by which each distinguished magnitude (level) of treatment effects (from 0-9, inclusive) is represented; and moreover, is represented by a configuration falling into the lowest side effects level available at that treatment effects magnitude. This provides a potential advantage for selecting from among available choices by treatment effects level. FIG. 8E, in contrast, shows choice by an alternative rule where each side effects level (along path 214B corresponding to linear path 214A) is represented by a configuration giving the largest available treatment effects level in its band. This provides a potential advantage for selection from a range of configuration options according to side effects level.

As to ordering of the device configurations for control: optionally (FIG. 8D), the ordering is between a "least treatment effects" configuration 240, and a "most treatment effects" configuration 242. The ordering is indicated by segments along path 244 which join the configurations to one another. In FIG. 8E, path 214B joins configurations from "least side effects" to "most side-effects". It should be noted that these rules do not necessarily produce the same ordering even when all configurations available are the same. In a simple case, there would usually be little preference to allow greater side-effect with less treatment effect, but where there are additional trade-offs involved, such a preference might prevail. Optionally, another ordering rule is used; for example a weighted combination of treatment effects and target effects. In terms of "control space" vs. "patient performance space", this could comprise defining an control space as an oblique line cutting across two or more dimensions of performance space. Configuration selection is optionally performed by stepwise movement through the ordered list of configurations available, for example as described in relation to FIGS. 7A and/or 8A.

In the foregoing, the evaluation scales of treatment effects and side effects have been treated as being substantially in opposition to one another. However, it is possible, in some embodiments, for evaluation scales to simultaneously represent wanted or unwanted effects (for example, two treatment effects or two side effects which are obtained at least partially in the alternative). In some embodiments, for example, device configurations provided for selection are optionally selected to obtain the highest available level of a second treatment effect, given a particular target level of a first treatment effect.

Multiple Patient Performance Parameter Configuration Selection

In the examples of FIGS. 8A-8E, a linear axis of control is provided through a one- or two-dimensional patient performance space. It can be understood also that there may be more than two evaluation scales for patient performance that apply to the operation of an implantable medical device. Optionally, this is dealt with by the use of any appropriate weighting scheme to make selections of device configurations available for selection, and an ordering among them along which selection is made.

It is, in the case of two or more evaluation scales, a potential advantage for one of the scales to be considered dominant, particularly with respect to arranging device configurations in an order for selection from, for example, as described in relation to FIG. 8A.

In some embodiments, control is also exercised along a plurality of axes.

Figure 8F:
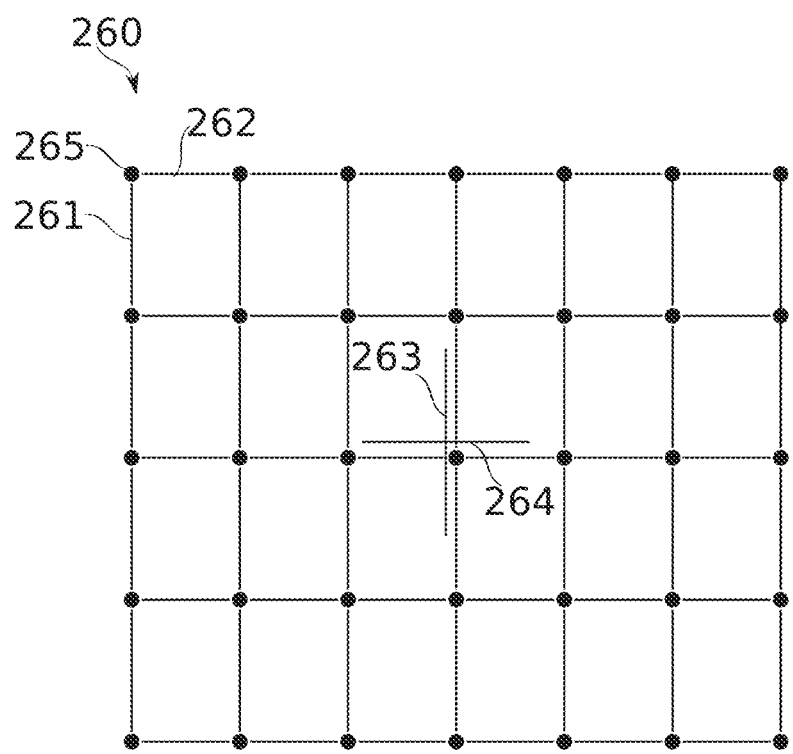
FIGS. 8F-8G schematically represent two-dimensional control spaces, according to some embodiments of the present disclosure.
Figure 8G:
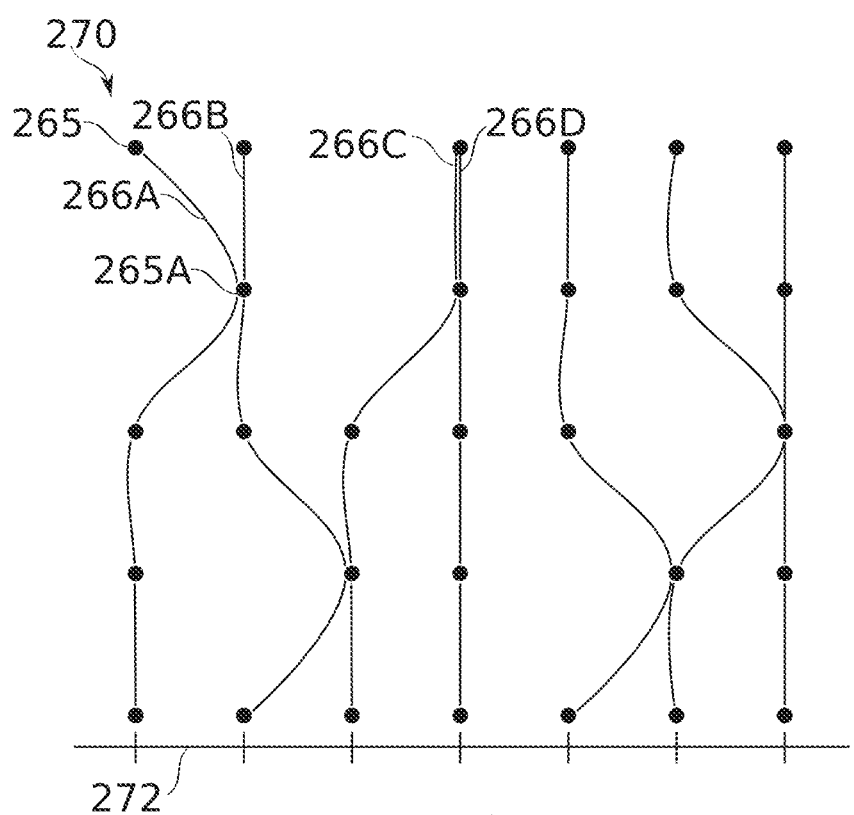

Reference is now made to FIGS. 8F-8G, which schematically represent two-dimensional control spaces 260, 270.

For purposes of explanation, the control spaces are shown as comprising a number of discrete selectable configurations 265. Optionally, however, configuration to is continuously selectable along one or more control axes, for example, control axes 263 and/or 264.

In a two- or higher-dimensional control space, there is optionally no longer a single ordering of selectable configurations 265 with respect to one another. However, edges such as edges 262, 261 optionally represent relative ordering along each axis 263, 264. Optionally, selection is set along two or more axes simultaneously. For example, a first axis optionally governs a magnitude of treatment effect, while a second axis optionally governs a relative trade-off between two or more side-effects.

FIG. 8F suggests control occurring within a more or less isomorphic grid.

However, this is only one possible control topology. As another example, FIG. 8G illustrates a case where some of the configurations which the overall extent of the control grid suggests are unavailable for some reason. For example, an unavailable configuration may represent a configuration which is physically unavailable to the device, is contraindicated, and/or is not validated. In some embodiments, this is handled by implementing a number of control "tracks" (such as control tracks 266A-266D), which at some positions share configuration points, but which are generally separate, and optionally selected among by use of another control axis 272. It should be understood that a selectable control track model is also optionally provided even for a fully populated grid. In some embodiments, a plurality of control tracks is provided which each pass through patient performance space along independent (optionally crossing) paths.

For example, the configuration options are optionally selected according to different rules (such as described in relation to FIGS. 8A-8E) for each track. This is a potential advantage, for example, when the patient performance parameter(s) of greatest concern are at least partially undetermined in advance (during device calibration), but become clearer as the patient learns to live with the device, and/or as the clinical situation evolves. Optionally, track switching is facilitated by tracks sharing one or more device parameter configurations in common, such as device configuration 265A.

Implantable Medical Device Configuration Methods

Figure 9A:
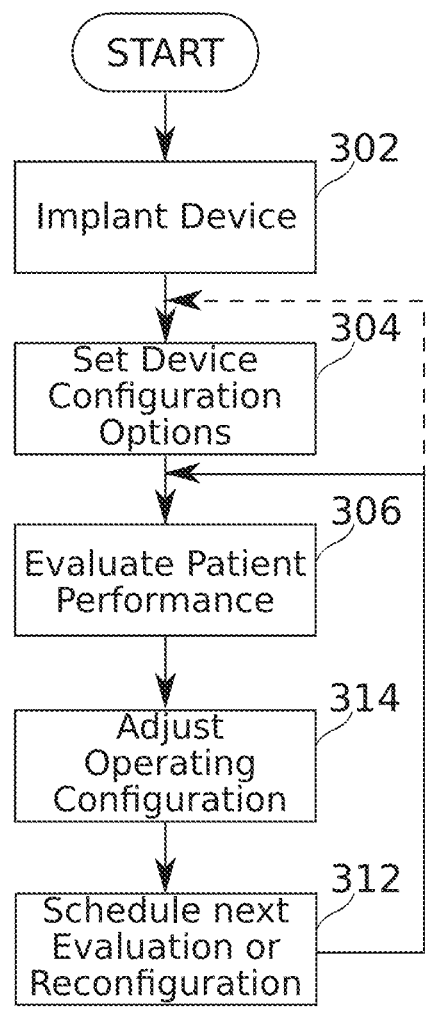
FIG. 9A is a flow chart representing a configuration life cycle of an implantable medical device, according to some embodiments of the present disclosure.

Reference is now made to FIG. 9A, which is a flow chart representing a configuration life cycle of an implantable medical device 40, according to some embodiments of the present disclosure.

At block 302, in some embodiments, an implantable medical device 302 is implanted.

At block 304, in some embodiments, device configuration options are set. Sub-operations associated with block 304 are detailed in relation to FIGS. 11A and 11B herein. Optionally, there is a distinction between initial setting of configuration options for the device (described, for example, in relation to FIG. 11A), and configuration option updates for the device (described, for example, in relation to FIG. 11B).

At block 306, in some embodiments, patient performance is evaluated. Evaluation of patient performance is described, for example, in relation to FIG. 10 herein. In some embodiments, evaluation of patient performance is performed by a primary care physician.

At block 314, in some embodiments, the operating configuration 42C of the device is adjusted. Adjustment optionally comprises operation of a user interface of a configuration selector 43, for example as described in relation to FIG. 7A, herein. In general, adjustment of the operating configuration 42C of the device is within a control space coordinated to a patient performance space.

The coordination is optionally such that a certain control setting corresponds to a certain targeted effect of the implanted medical device 40 in patient performance space. Optionally, the coordination is such that selection comprising movement in a particular direction in control space produces a corresponding movement of the device's effects in patient performance space. For example, a given direction of control movement is optionally tied to increasing how readily a pacing rate of a patient's heart is increased in response to sensed data (e.g. acceleration) indicating activity. Optionally, the technical parameters underlying this increased sensitivity include a plurality of parameters; for example, one or more of thresholds of acceleration, sensing integration time, maximum allowable pacing rates, rate of pacing ramp-up, etc.

Figure 11A:
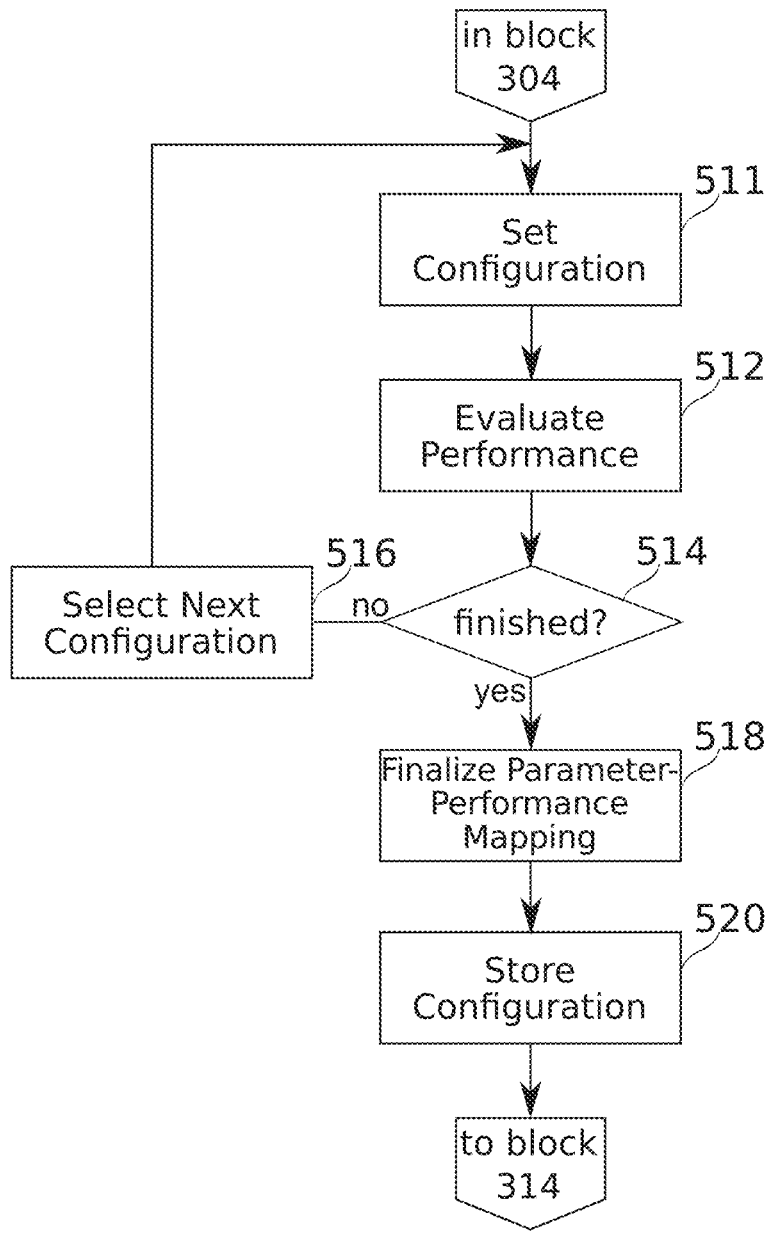
FIG. 11A is a flowchart that schematically represents a method of setting available configuration options for an implantable medical device, according to some embodiments of the present disclosure.
Figure 11B:
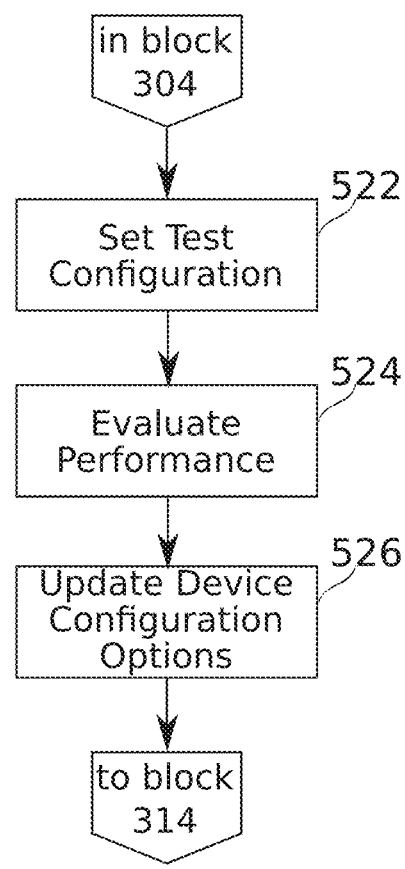
FIG. 11B is a flowchart that schematically represents a method of updating available configuration options for an implantable medical device, according to some embodiments of the present disclosure.

At block 312, in some embodiments, a next patient performance evaluation (that is, a re-entry to the flowchart at block 306) and/or a next reconfiguration of the device (re-entry to the flowchart at block 304, optionally corresponding to the flowchart of FIG. 11B) is scheduled.

Figure 9B:
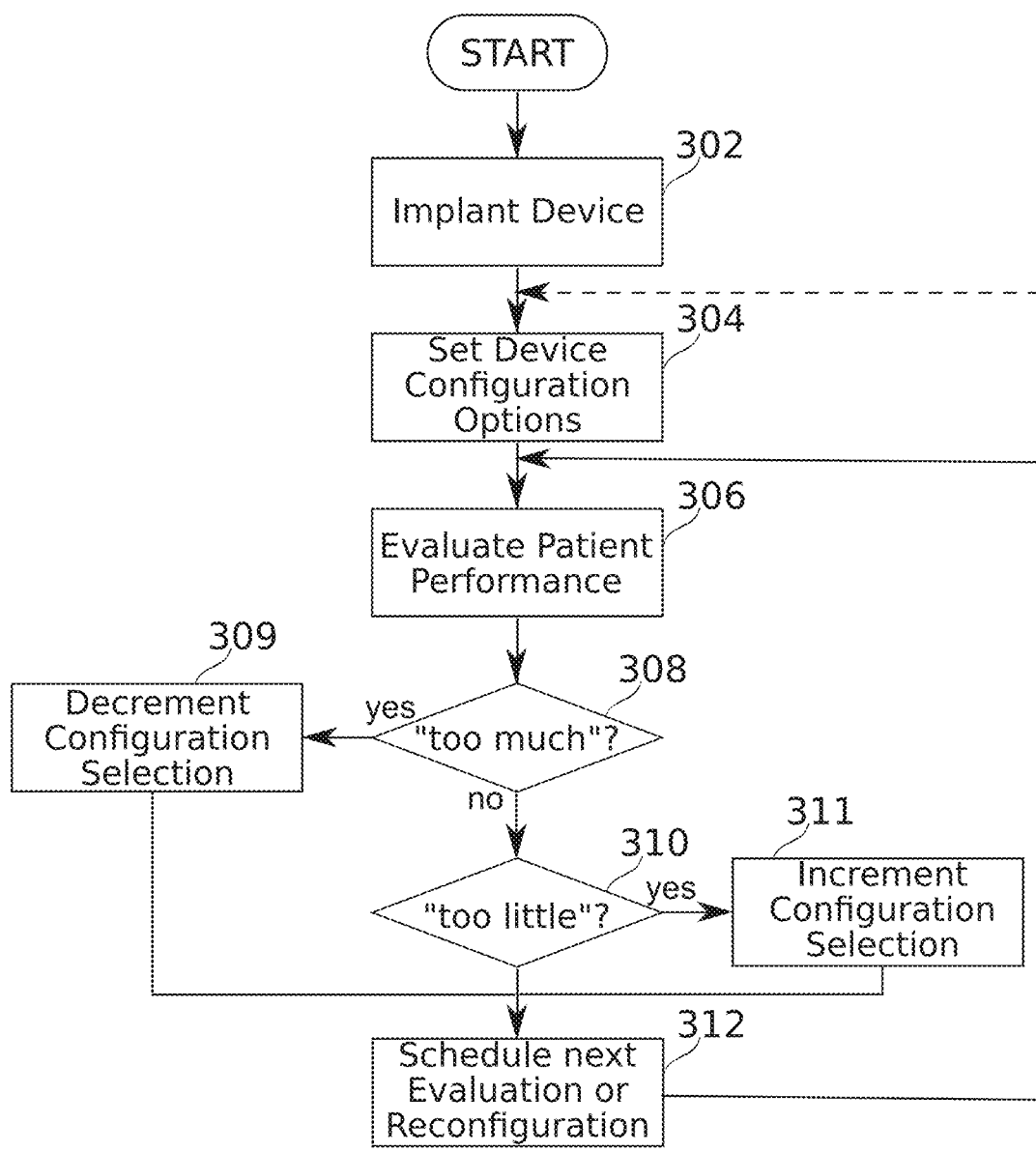
FIG. 9B is a flow chart representing a more particular configuration life cycle of an implantable medical device, according to some embodiments of the present disclosure.

Reference is now made to FIG. 9B, which is a flow chart representing a more particular configuration life cycle of an implantable medical device 40, according to some embodiments of the present disclosure.

In some embodiments, configuration control of an implanted medical device is realized by implementation of a simple decision to operate the device with more or less of some effect, or with the configuration unchanged. This control scheme corresponds, for example, to control by moving in one direction or another along a path and/or parametric function, for example as described in relation to FIGS. 8A-8E.

Blocks 302, 304, 306, and 312, in some embodiments, occur substantially as described in relation to FIG. 9A. Blocks 308-311 comprise an example of a more specific implementation of block 314 of FIG. 9A.

At block 308, in some embodiments, a determination is made, based on the patient performance evaluation of block 306, as to whether or not less of some effect (treatment effect or side-effect, according to the device configuration) is needed (that is—the question "is there too much of the effect?" is answered).

If so, the configuration selection is decremented at block 309 (decremented in the direction of reduced effect). Otherwise, at block 310, a determination is made as to whether or not more of the effect is needed (there potentially being too little of it). If so, at block 311, the configuration selection is incremented.

Optionally, these operations are performed by a selection between two button presses, for example, "+" and "-", to change a selected device parameter configuration. A potential advantage of this particularly simple control regime is that it can be fairly easily implemented by a primary care physician after an introductory familiarization with the device. Preferably, the patient performance parameter behind to the "too much" and "too little" questions is easily determined by the physician in consultation with the patient and/or based on common test results.

Figure 10:
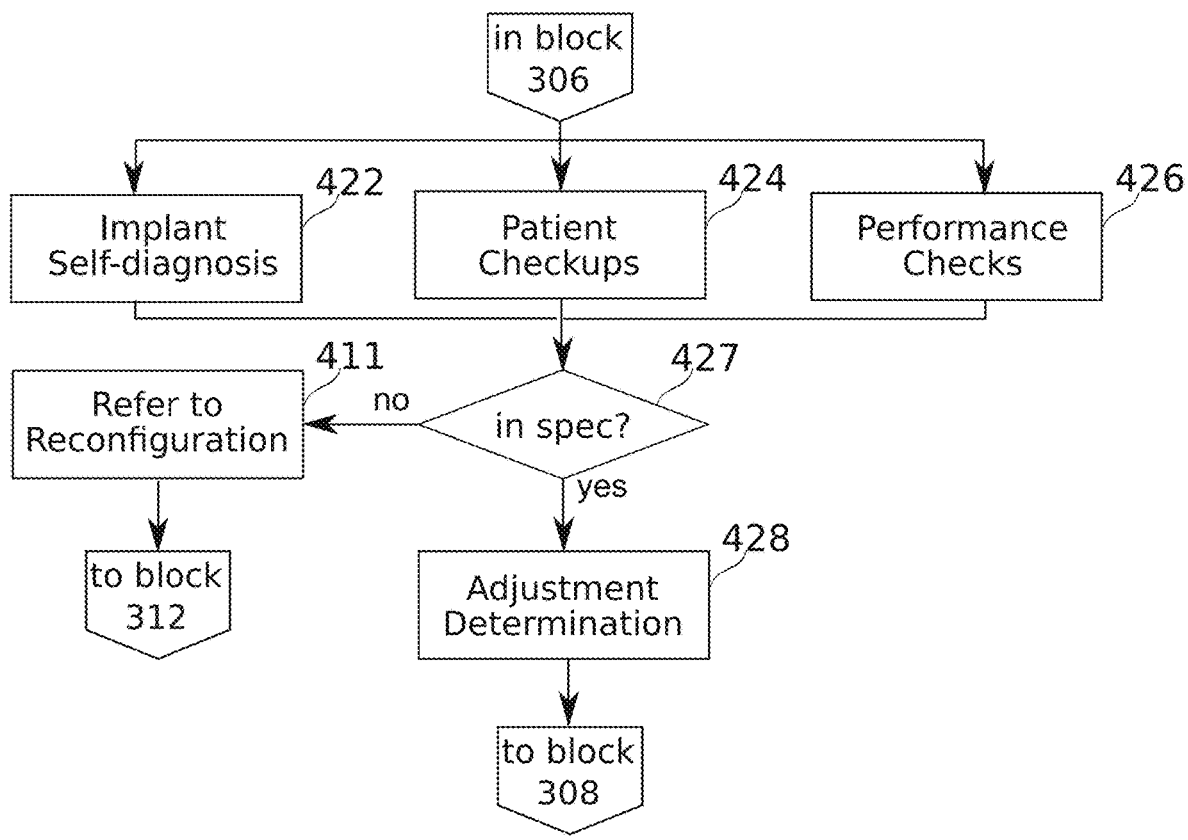
FIG. 10 is a flowchart that schematically represents operations of patient performance evaluation, according to some embodiments of the present disclosure.

Reference is now made to FIG. 10, which is a flowchart that schematically represents operations of patient performance evaluation, for example, in the context of block 306 of FIGS. 9A-9B.

In some embodiments, information about patient performance is obtained from any one of three potential sources implant self-diagnosis 422, patient checkups 424, and device performance checks 426. These can be distinguished, for example, as information which an implanted device 40 determines about itself (block 422), and optionally provides to itself for further action; information which a physician determines about patient performance in consultation with the patient and/or test results outside the device itself (block 424); and information which a physician determines together with controlled operation of the device (block 426).

At block 422, in some embodiments, implanted medical device self-diagnosis is performed. Optionally, self-diagnosis comprises determining (based on sensed patient performance data provided to the device) what the performance effects of device operation are for one or more particular device operating configurations.

Optionally, the self-check operates by comparing the routine operation of the device to the results expected, for example, as established during device calibration.

Optionally, self-diagnosis comprises occasional operation outside the routine configuration, and monitoring of the result (this is also described, for example, in relation to block 522 of FIG. 11B).

Optionally, the implanted medical device adjusts itself based on results.

Additionally or alternatively, it is configured to report status results (for example, detection of changes, calibration skew, etc.) through an appropriate control interface 43A.

At block 424, in some embodiments, a patient checkup is performed. The patient checkup optionally comprises any observation of a patient by a physician or clinic; for example, a test result (e.g., metabolite level, and/or monitoring data), a symptom, vital statistic changes, lifestyle satisfaction, incidence of infrequently triggered events, and/or another clinical finding. However, typically, the observation to is of a performance parameter suitable for routine evaluation by a primary physician during a routine checkup.

At block 426, in some embodiments, implanted device performance checks are performed. These optionally comprise issuance by the evaluating physician of any suitable command to the medical device, coupled to observation of the results.

Optionally, an implanted medical device makes available a mode wherein it can be set into one or more evaluation configurations. For example, an evaluation mode for a pacing device optionally sets one or more pacing configurations that differ from the baseline configuration. Evaluation optionally comprises verifying that the performance results expected are those actually obtained (for example, by separate monitoring of heart rate). In some embodiments, no entry into a reserved test mode is performed; rather, the patient is directly guided through a suite of tests (e.g., exercises) designed to elicit responses from the implanted device which should be revealed in the observation of one or more patient performance parameters.

Preferably, the operations of block 422, 424, and 426 are arranged to require minimal specific expertise from the physician regarding operation and configuration of the device 40 itself. Preferably, these operations chiefly or solely consist of the device adjusting itself, and the physician interacting as they would normally with the patient in order to understand the current performance state of the patient.

At block 427, in some embodiments, the data gathered at one or more of blocks 422, 424, and 426 is evaluated to determine if the implant is operating within specified and/or targeted parameters.

This is optionally accomplished by use of the device itself (for example, the device reports on itself as being within or not within specifications based on self-test result). If the device is found to be sufficiently out of specification, the patient is optionally referred to a device specialist for reconfiguration of the device (block 411).

At block 428, in some embodiments, a determination is made as to whether or not the configuration of the device should be adjusted (via configuration selector 43). Criteria for adjustment are described, for example, in relation to block 306 of FIG. 9A.

Reference is now made to FIG. 11A, which is a flowchart that schematically represents a method of setting available configuration options for an implantable medical device, according to some embodiments of the present disclosure.

At block 511, in some embodiments, an iterating loop is entered in which a device operating configuration is set, evaluated, changed, and evaluated again.

Optionally, any one or more of several strategies governing the selection is used.

In some embodiments, configuration options are chosen at least in part according to one or more clinical targets for the patient, together with an understanding of how a device's parameter settings work together to achieve clinical targets. Optionally, the clinical target is anticipated to change over time, and configuration options are selected so that new targets are achieved. For example, if a patient performance effect of a device is to assist in weight loss (for example, by modulation of autonomic responses), an initial clinical target is optionally selected to be a high rate of weight loss, an intermediate clinical target is a more sustainable rate of weight loss, and a long term clinical target is maintenance of a target weight.

The choice device configuration for achieving a clinical target optionally comprises an iterative approach, for example, for devices where inter-patient variability leads to at least some initial lack of predictability in the magnitude of the effects of device operation.

A simple, but potentially laborious (or even impractical) strategy is to iteratively select each of a range of possible device configurations which are candidates for configuration options, install them on the device (for example, using device programmer 63), and evaluate the result (for example, as described at block 512).

A potentially less intensive procedure comprises selection of a few "landmark" configuration options, evaluating them with respect to patient performance (for example as described in relation to block 512), and then calibrating other configuration options to patient performance based on their anticipated effects on patient performance relative to the landmark configurations. This is particularly suited for the calibration of configuration options where patient performance change is expected to be substantially monotonic (for example, linear) between two landmark configurations. It is also possible for more complex configuration characteristics to be set this way, for example, according to a default mapping between configuration options and patient performance determined based on experience with other patients, with the same patient, and/or based on theoretical considerations. Aspects of this approach are described, for example, in relation to FIG. 12.

At block 512, in some embodiments, the effects of a configuration set at block 511 are evaluated in terms of some measure of patient performance appropriate to the treatment effects and/or side effects which the device is expected to produce in the patient. The testing optionally comprises, for example, any appropriate test and/or indication of activity, responsiveness, metabolite level, patient comfort, or other indication, as appropriate to the type of device implanted. The testing optionally comprises direct input-output testing (adjust device, measure a resulting change). The testing optionally comprises perturbation and/or stress testing, for example, measurement of a response to exercise, food consumption or fasting, drug injection, or another manipulation which tests how an implanted device operates within a certain regime of interest.

In some embodiments, a measure of patient performance used in calibration is different than a measure used as a part of long term device operation adjustment.

Optionally, calibrations for the purpose of establishing device configuration options are performed in a specialist-accessible patient performance space.

Optionally, the patient performance space which forms a basis for adjustment long-term is based on parameters more suited to the evaluation of a primary care physician, such as vital statistic changes, lifestyle satisfaction, incidence of infrequently triggered events, etc. In some embodiments, the two performance spaces are established in an initial registration according, for example, to past experience, and/or theoretical considerations. In some embodiments, a device is calibrated according to specialist-accessible patient performance parameters to give a range of device configuration options which are expected to encompass the preferred region of a patient performance space used in long-term evaluations.

More particularly, during calibration of a device, it may not be possible, practical, and/or preferred to evaluate patient performance using the same patient performance metrics as are available over the course of a longer period of time (for example, as available in relation to the operations of block 306). For example, a patient is treated by neuromodulatory stimulation, in some embodiments, to achieve weight loss over a period of several months or more. Over that period, the performance parameter of weight loss is relatively straightforward to measure.

During initial calibration, however—which preferably involves checking of several configuration options within a few hours to days—this might not be practical.

Evaluation of some patient performance characteristics is potentially dependent on the daily routine of the patient, and/or on how the patient experiences relative advantages and limitations of different treatment levels. For example, a heart patient whose lifestyle requires regular exertion (stair climbing, for example) might be less tolerant of limitations on maximum heart rate than a patient which is more sedentary. A patient being treated for pain by neuromodulation might not clearly conceive of how a particular tradeoff between reduced pain and side-effect sensations (such as tingling) will affect their normal activities, until they return to them.

In contrast, it might be practical, during device calibration, to take advantage of relatively sophisticated, complex, and/or invasive test procedures which are not generally available outside of a specialist clinic, are potentially risky, and/or are too resource intensive to use in long-term monitoring. For example, radio imaging is optionally used to monitor metabolic activity in response to a neuromodulation device. ECG monitoring is optionally used to detect heart activity in response to stress testing.

Whatever the evaluation method used, a result of the evaluation at block 512, in some embodiments, is to place a particular device operation configuration (defined in device configuration space) in some patient performance space.

At block 514, in some embodiments, it is determined whether or not all test configurations have been evaluated. If not, the next configuration is optionally selected at block 516 (strategies used for this selection are described in relation to block 511), and flow returns to block 511.

At block 518, in some embodiments, the accumulated data relating device configurations to patient performance is converted into device configuration option data 41. Some features of device configuration option data 41 are described, for example, in relation to FIGS. 7A-7B, herein.

At block 520, in some embodiments, the device configuration option data 41 are stored in the device, for example, by use of a programmer 63.

At this stage, the configuration of the device can optionally be understood within the following framework:

A control space is exposed through one or more interface controls of configuration selector 43. The controls adjust and/or select a position in this control space.

The selection or adjustment in control space indicates a corresponding position or adjustment in a primary care patient performance parameter space. This parameter space comprises measurable patient performance parameters on which future adjustment of the device will be based.

Furthermore, the selection or adjustment in control space operates to choose an operating configuration 42C, based on the provided device configuration option data 41.

From an external standpoint, some of the complexity of device operation configuration is thereby masked behind relatively simple determinations and decisions based on patient performance parameters.

Additionally and/or optionally:

There can be at least one additional "specialist" or calibration patient performance space. This is optionally used during initial setup of the device, and/or referred to during subsequent updates and/or re-calibrations of the device. The control space exposed through configuration selector 43 may or may not correspond to the calibration patient performance space. However, there is preferably enough of a correspondence between the two types of patient performance spaces that results in one can be alternatively understood as indicative of likely results in the other.

Reference is now made to FIG. 11B, which is a flowchart that schematically represents a method of updating available configuration options for an implantable medical device, according to some embodiments of the present disclosure.

In some embodiments, the calibration of a device 40 is potentially subject to change. For example, there may be changes in the clinical situation and/or lifestyle of a patient, and/or interactions with routine activities of a patient not fully appreciated during calibration. Optionally, the most relevant patient performance parameter (for example, a rate of weight loss for neurostimulation aimed at weight reduction) is not measurable outside of a period of several weeks or months elapsing after the device is initially configured. Optionally there is a requirement to correct for drift in device operation; for example, if a quality of stimulation target contact changes over time.

Optionally, re-calibration is performed according to a regular maintenance schedule, or otherwise as appropriate, for example, as described with respect to block 428 of FIG. 10 (e.g., based on the results of device diagnostics, and/or care provider observations). In some embodiments, a device at least partially self-recalibrates from time to time based on an internal schedule, observations of increasing skew between expected and measured results, and/or upon receiving control instructions to do so.

At block 522, in some embodiments, device re-calibration begins, and a test configuration is selected. In addition to any one of the test strategies described in relation to FIG. 11A, an option available for test configuration strategy comprises comparing current results for the patient against older calibration test results—all results, or a portion thereof. This is well-adapted to mapping-type calibration described in relation to FIG. 12 (for example, an old map is transformed as necessary to create a new one).

In some embodiments, a self-calibrating device is configured to receive data reflecting one or more patient performance parameters through sensors (its own, or sensors it connects to). Optionally, these sensors are used to provide the patient performance data needed for calibration. For example, a self-calibrating device is optionally operable to provide a triggering stimulus to an active tissue (muscular or neural tissue, for example), where it is preferable that the triggering stimulus be minimal, that the resulting activity have some particular measurable feature (duration, latency, or rise time, for example), or where some other quantifiable criterion can be set based on data received from sensing. Then self-calibration optionally comprises a deliberate variation of the triggering stimulus or other output (probing output), determination of the response level, and corresponding adjustment so patient performance and device parameter configuration remain in synchronization.

In some embodiments, this procedure is optionally performed during initial setup of the device (for example, as part of the loop of blocks 511, 512, 514, and 516 of FIG. 11A). Optionally, this allows the device to at least partially "teach itself" about how the device parameter domain and the patient performance domain align with one another.

It should be understood that where a device is allowed to perform such self-calibrations, the range of available probing outputs is confined to those which are considered safe, and/or self-calibration is limited to times when the patient is in under adequate supervision for the management of any unexpected side effect or adverse result.

In some embodiments, there is feedback into the original calibration procedure based on adjustments made later in the lifetime of the device. For example, if there is found to be a degree of delayed physiological adaptation to device operation (e.g., stimulation by a device becomes more or less effective over time as a patient's body adapts to it); the calibration procedure is optionally updated to anticipate this effect.

At block 524, in some embodiments, corresponding patient performance is evaluated. In some embodiments, there is a loop among several test configurations and according to test calibration strategy, (for example as described in relation to FIG. 11A), but this detail is elided from FIG. 11B for simplicity of description.

At block 526, in some embodiments, the device configuration options are updated on the device 40, for example as described in relation to block 520 of FIG. 11A.

In some embodiments, the updating optionally comprises the identification of device configurations which should be excluded from future selection. This can be based on patient-physician interactions and clinical evaluation, and/or on the device's own self-reporting. For example, if the device has recorded a triggering event (such as an epoch of atrial fibrillation) which occurred during device operation under some particular configuration, that configuration is optionally flagged for avoidance in future selections. In some embodiments, this allows the definition of one or more "red zones", which potentially comprise and/or allow triggering conditions specific to the individual patient.

Figure 12:
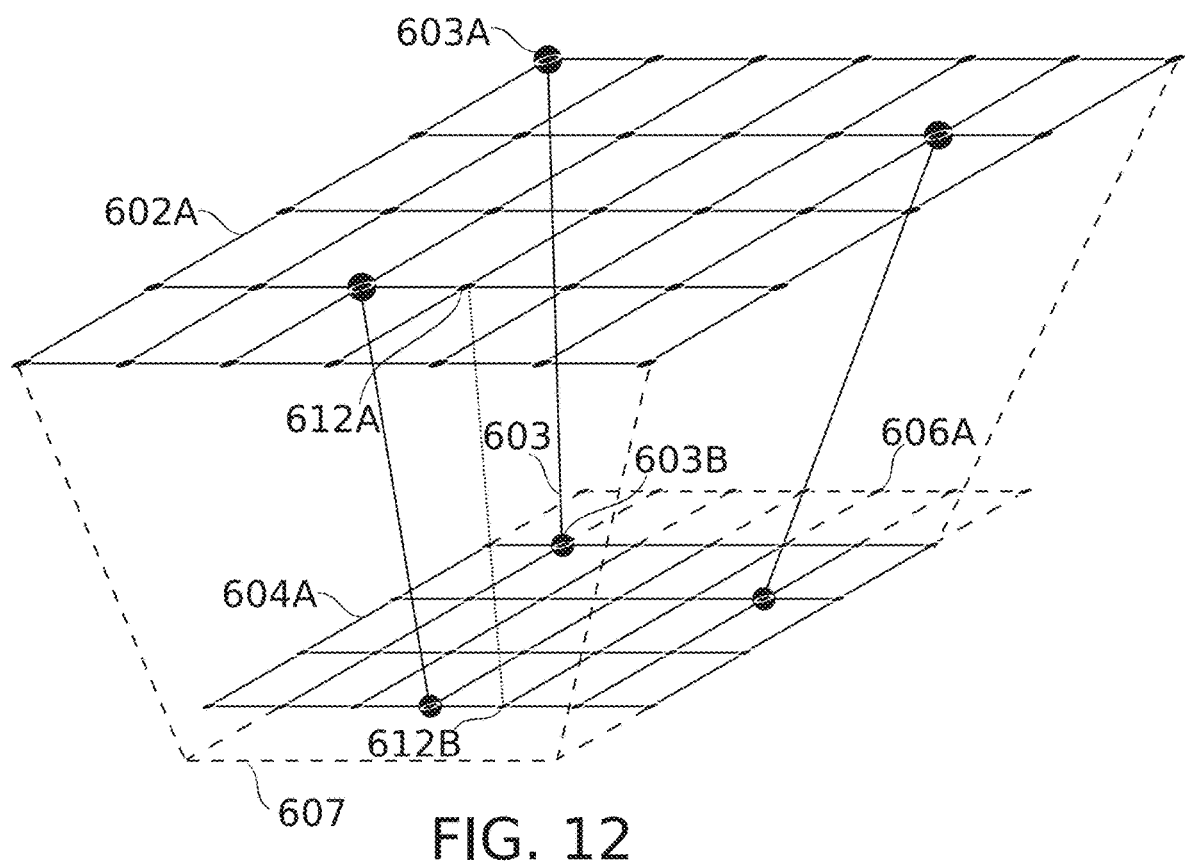
FIG. 12 schematically represents conversion of a default mapping of device parameter space to patient performance space to a mapping applicable to a particular patient, according to some embodiments of the present disclosure.

Reference is now made to FIG. 12, which schematically represents conversion of a default mapping 602A of device parameter space to patient performance space to a mapping 604A applicable to a particular patient, according to some embodiments of the present disclosure.

In some embodiments (for example, as described in relation to block 518 of FIG. 11A herein), determination of device configuration option data comprises conversion of a default mapping 602A of a device parameter space to patient performance space to a mapping 604A usable with a particular patient. A potential advantage of this approach is to reduce configuration testing required with each individual patient, while still providing a large number of usable options for adjustment.

Default mapping 602A, in some embodiments, optionally comprises an array of device configuration options (including options 612A, 603A, for example), each corresponding to a particular operating configuration of the device, as well as at least a relative location in patient performance space. Default mapping 602A is optionally developed, for example, based on data gathered from one or more patients, on to interpolations and/or extrapolations from this data, and/or from relative effects expected based on knowledge of the effects of one or more device parameter settings. Optionally, there are a plurality of default mapping "templates" available, each suited to a different clinical situation; optionally, the correct default mapping is selected based on characteristics of the patient (age, weight, gender, and/or disease state, for example), and/or based on which default mapping seems most appropriate based on test results obtained during calibration itself.

The mapping to patient performance space is optionally only relative. That is: there is not necessarily a particular patient performance expectation defined by a location within the default mapping; rather, what the default mapping defines is how performance changes among different device configuration options. For purposes of illustration, what is shown in FIG. 12 comprises discretely mapped device configurations. However, it should be understood that mapping is optionally continuous and/or discontinuous.

In some embodiments, conversion of default mapping 602A to a mapping 604A usable within the performance space of a particular patient is performed by testing one or more landmark configurations (for example, configuration 603A, and/or other configurations marked by dark spheres on default mapping 602A), and observing actual patient performance results, for example as described in relation to FIG. 11A. This directly defines positions in patient performance space such as configuration 603B in mapping 604A (indicated as identical in device configuration to configuration 603A by connecting line 603).

Optionally, these test configuration mappings define a transformation by which other configuration conversions, such as between configuration 612A and 612B are performed. Optionally, patient performance in configuration mapping regions (such as region 606A) outside the space of the transformed default mapping is determined by actual testing, and/or by extrapolation. Optionally, part of the default mapping 602A (such as region 607) does not map into patient performance space, for example, due to the particular physiology of the patient.

In some embodiments, occasional re-calibration of the relationship of device configurations to patient performance follows a similar model. For example, mapping 602A optionally comprises a current mapping of a particular patient's performance space to available device configuration options, and this mapping is converted to new mapping based on re-calibration, for example as described in relation to FIG. 11B.

General

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. An implantable medical device system supporting configuration by a primary care physician, comprising:
   the implantable medical device;
   a data store configured to receive and store a plurality of inactive technical parameter sets for use with the implantable medical device;
   wherein the implantable medical device provides a plurality of functions accessible over a communication link, including a function comprising parameter set activation;
   the parameter set activation comprising activation of least one of the plurality of inactive technical parameter sets to change device-domain parameters controlling therapeutic operation of the device;
   a plurality of access keys, each recognizable to obtain access to a respective at least one of the plurality of functions; and
   a selection interface for selecting from among the inactive technical parameter sets and activating at least one of them via the parameter set activation function;
   wherein the implanted medical device provides communication link access to the function allowing parameter set activation based on recognition of one of the plurality of access keys, validated through the implanted medical device; and the access is allowed based on which access key of the plurality of access keys is recognized.

2. The implantable medical device system of claim 1, wherein the data store indexes the technical parameter sets according to a parameter of their effect on patient performance, and the selection interface presents inactive technical parameter sets for selection according to the index.

3. The implantable medical device system of claim 1, wherein the data store is integrated with the implanted medical device.

4. The implantable medical device system of claim 1, wherein the access key comprises an alphanumerically represented key.

5. The implantable medical device system of claim 1, wherein the access key comprises a cryptographic key.

6. The implantable medical device system of claim 1, wherein the access key comprises a charger device.

7. The implantable medical device system of claim 1, wherein the access key comprises the data store.

8. The implantable medical device system of claim 1, wherein operation of the selection interface comprises entering data about the operation of another implantable medical device of the patient.

9. The implantable medical device system of claim 1, wherein operation of the selection interface comprises entering data about a medicament prescription of the patient.

10. The system of claim 1, wherein, for at least one of the plurality of the access keys, the respective at least one of the plurality of functions does not include the parameter set activation function.

11. A method of associating an implanted medical device to a non-implanting referring health care provider, comprising:
    providing the referring health care provider with one of a plurality of device access keys, each recognizable to obtain access to a respective at least one of a plurality of functions of the implanted medical device accessible over a communication link;
    the plurality of functions including a function comprising parameter set activation;
    the parameter set activation comprising activating least one of a plurality of inactive technical parameter sets to change device-domain parameters controlling therapeutic operation of the device;
    configuring the implanted medical device to allow communication link access to the parameter set activation function, wherein the configuring includes recognizing the device access key, including:
       validating the device access key through the implanted medical device, and
       identifying which access key of the plurality of access keys is recognized; and
    activating at least one of the plurality of inactive technical parameter sets.

12. The method of claim 11, wherein the implanted medical device is configured to allow selection of the inactive technical parameter set being activated from among a plurality of technical parameter sets preconfigured for use with the implantable medical device.

13. The method of claim 12, wherein the configuring comprises receiving an identifier of the device access key from the referring health care provider, and configuring the device to recognize the identifier.

14. The method of claim 11, wherein the configuring comprises the referring health care provider configuring the device to recognize an identifier of the device access key.

15. The method of claim 11, wherein activation of the inactive technical parameter set enables an inactive treatment function of the implanted medical device.

16. The method of claim 15, comprising locking the device to inactivate the inactive technical parameter set until accessed by the device access key.

17. The method of claim 11, wherein the device access key comprises a charging mechanism for charging the implanted medical device.

18. The method of claim 11, wherein the device access key is limited in a number of uses.

19. The method of claim 11, wherein the device access key comprises at least one of an alphanumeric code and a cryptographic key.

20. The method of claim 11, wherein, for at least one of the plurality of the access keys, the respective at least one of the plurality of functions does not include the parameter set activation function.

* * * * *